US005470753A

United States Patent [19]
Sepetov et al.

[11] Patent Number: 5,470,753
[45] Date of Patent: Nov. 28, 1995

[54] PEPTIDE SEQUENCING USING MASS SPECTROMETRY

[75] Inventors: Nikolai Sepetov; Olga Issakova; Viktor Krchnak; Michal Lebl, all of Oro Valley, Ariz.

[73] Assignee: Selectide Corporation, Tucson, Ariz.

[21] Appl. No.: 68,947

[22] Filed: May 28, 1993

Related U.S. Application Data

[63] Continuation-in-part of Ser. No. 939,811, Sep. 3, 1992, abandoned.

[51] Int. Cl.[6] .................................................. G01N 33/00
[52] U.S. Cl. ........................... 436/89; 436/173; 530/300; 530/333; 530/344
[58] Field of Search ..................... 436/89, 173; 530/300, 530/333, 344

[56] References Cited

U.S. PATENT DOCUMENTS

| | | | |
|---|---|---|---|
| 4,093,855 | 6/1978 | Fite et al. | 250/282 |
| 4,224,031 | 9/1980 | Mee et al. | 23/250 B |
| 4,701,419 | 10/1987 | Morris | 436/89 |
| 5,103,093 | 4/1992 | Sakairi et al. | 250/288 |
| 5,130,538 | 7/1992 | Fenn et al. | 250/282 |
| 5,221,518 | 6/1993 | Mills | 422/62 |

FOREIGN PATENT DOCUMENTS

| | | |
|---|---|---|
| 2648230 | 12/1990 | France. |
| WO90/05192 | 5/1990 | WIPO. |

OTHER PUBLICATIONS

Anderegg et al., "Probing helical content of peptides by duterium exchange electrospray mass spectrometry," The 40th ASMS Conference on Mass Spectrometry and Allied Topics, pp. 475–476.

Bartels, "Fast Algorithm for peptide sequencing by mass spectroscopy," Biomedical and Environmental Mass Spectrometry 19:363–368 (1990).

Bertrand et al., "Computer–aided sequence determination of peptides: A comparative study of structural information obtained from LSIMS and electrospray mass spectra," The 40th ASMS Conference on Mass Spectrometry and Allied Topics, pp. 1503–1504.

Biemann, "Mass spectrometric methods for protein sequencing," Analytical Chemistry 58(13):1288A–1300A (1986).

Biemann et al., "Mass spectrometric determination of the amino acid sequence of peptides and proteins," Mass Spectrometry Reviews 6:1–76 (1987).

Biemann, "Sequencing of peptides by tandem mass spectrometry and high–energy collision–induced dissociation," Methods in Enzymology 193:455–479 (1990).

Bodnar et al., "Sequence analysis of a sexual receptivity–terminating factor in the corn earworm moth and peptides associated with the class I MHC molecule, HLA–B7," The 40th ASMS Conference on Mass Spectrometry and Allied Topics, pp. 1803–1804.

Costello et al., "Recent progress in the determination of structures of large biomolecules", pp. 190–191.

Cox et al., "Sequence and functional characterization of peptides associated with the class I MHC molecule HLA–A2.1," The 40th ASMS Conference on Mass Spectrometry and Allied Topics, pp. 1805–1806.

Foti et al., "Sequencing of peptides containing alanine, asparagine, histidine, isoleucine, and tryptophan by partial methanolysis and fast atom bombardment mass spectrometry," Biomedical and Environmental Mass Spectrometry 20(6):345–350 (1991).

Ishikawa et al., "Computer–aided peptide sequencing by fast atom bombardment mass spectrometry," Biomedical and Environmental Mass Spectrometry 13:373–380 (1986).

Johnson et al., "Computer program (SEQPEP) to aid in the interpretation of high energy collision tandem mass spectra of peptides," Biomedical and Environmental Mass Spectrometry 18:945–957 (1989).

Kassel et al., "Primary structure determination of peptides and enzymatically digested proteins using capillary liquid chromatography/mass spectrometry and rapid linked scan techniques," Analytical Chemistry 63(11):1091–1097 (1991).

Kulik et al., "A reliable method for the amino acid sequence determination in tetrapeptides: A study on the positive and negative ion tandem mass spectra of tetrapeptides," Biomedical and Environmental Mass Spectrometry 20(9):553–558 (1991).

Lee et al., "MacProMass: A computer program to correlate mass spectral data to peptide and protein structures," Biomedical and Environmental Mass Spectrometry 19:639–645 (1990)

(List continued on next page.)

Primary Examiner—David A. Redding
Attorney, Agent, or Firm—Pennie & Edmonds

[57] ABSTRACT

The present invention relates to methods for determining the amino acid composition, and more preferably the sequence, of a peptide using mass spectrometric techniques. The method is particularly useful for sequencing peptides isolated from natural sources or from libraries of peptides that have been prepared synthetically, and for peptides that are not amenable to Edman degradation sequencing. In one embodiment, the method for determining the amino acid composition or sequence of a peptide comprises determining the difference of the mass of the peptide from the mass of a deuterium-hydrogen exchanged peptide, and from this difference determining the number of exchangeable (labile) hydrogen atoms (protons). Candidate peptides having amino acid compositions or sequences that do not contain the observed number of exchangeable protons are eliminated. In another embodiment, synthesis of a portion of the peptides in a library of peptides is terminated after each coupling step, whereby a set of sequentially truncated fragments of each peptide is formed. Thus the sequence of the peptide can be determined by determining the difference in the molecular weight between each peptide or fragment thereof and the sequentially smaller fragment of the peptide.

3 Claims, 11 Drawing Sheets

OTHER PUBLICATIONS

Matsuo et al., "Computer program PAAS for the estimation of possible amino acid sequences of peptides," Biomedical Mass Spectrometry 8 (4) :137–143 (1981).

Matsuo et al., "Improved PAAS, a computer program to determine possible amino acid sequences of peptides," Biomedical Mass Spectrometry 10(2):57–60 (1983).

McCloskey, "Introduction of deuterium by exchange for measurement by mass spectrometry," Methods in Enzymology 193:329–339 (1990).

Papayannopoulos et al., "Fast atom bombardment and tandem mass spectrometry of synthetic peptides and byproducts," Peptide Research 5(2):83–90 (1992).

Reddy et al., "Deuterium labeled 3–nitrobenzyl alcohol as a matrix for fast atom bombardment mass spectrometry," Biomedical and Environmental Mass Spectrometry 18:1087–1095 (1989).

Ronge et al., "Peptide sequencing by MS–MS techniques: A systematic study," *Recent Developments in Mass Spectrometry in Biochemistry, Medicine and Environmental Research*, A. Frageno, editor, Elsevier Scientific Publishing Co., Amsterdam, pp. 255–281 (1981).

Rosnack et al., "C–terminal sequencing of peptides using electrospray mass spectrospray," The 40th ASMS Conference on Mass Spectrometry and Allied Topics, pp. 1797–1798.

Sakurai et al., "PAAS 3: A computer program to determine probable sequence of peptides from mass spectrometric data," Biomedical Mass Spectrometry 11(8):396–399 (1984).

Scoble et al., "A graphics display oriented strategy for the amino acid sequencing of peptides by tandem mass spectrometry," Fresenius Z Anal Chem 327:239–245 (1987).

Siegel, "Applications of the peptide sequencing algorithm newps to fast atom bombardment and electrospray mass spectral data," The 40th ASMS Conference on Mass Spectrometry and Allied Topics, pp. 1785–1786.

Siegel et al., "An efficient algorithm for sequencing peptides using fast atom bombardment mass spectral data," Biomedical and Environmental Mass Spectrometry 15:333–343 (1988).

Stults, "Peptide sequencing by mass spectrometry," Biomedical Applications of Mass Spectrometry 34:145–201 (1990).

Suckau et al., "Conformation of gaseous multiply charged protein ions by H/D exchange in ESI/PTMS," The 40th ASMS Conference on Mass Spectrometry and Allied Topics, pp. 477–478.

Wagner et al., "Derivatives of peptides to enhance ionization effiency and control fragmentation during analysis by fast atom bombardment tandem mass spectrometry," 20:419–425 (1991).

Yates et al., "Computer aided interpretation of low energy MS/MS mass spectra of peptides," *Techniques in Protein Chemistry II*, by Academic Press, Inc. pp. 477–485 (1991).

Zhou et al., "Computer aided interpretation of low energy ESI/MS/MS spectra of peptides," The 40th ASMS Conference on Mass Spectrometry and Allied Topics, pp. 635–636.

Zhou et al., "Mass spectrometry software for biochemical analysis," The 40th ASMS Conference on Mass Spectrometry and Allied Topics, pp. 1396–1397.

5,470,753

PEPTIDE SEQUENCING USING MASS SPECTROMETRY

The present application is a continuation-in-part copending application Ser. No. 07/939,811, filed Sep. 3, 1992, now abandoned, which is incorporated herein by reference in its entirety.

FIELD OF THE INVENTION

The present invention relates to methods for determining the amino acid composition, and more preferably, the sequence, of a peptide using mass spectroscopy techniques. The method is particularly useful for sequencing peptides isolated from natural sources or from libraries of peptides that have been prepared synthetically, and for peptides that are not amenable to Edman degradation sequencing.

BACKGROUND OF THE INVENTION

Recent developments of new technologies provide libraries of peptides attached to solid phase supports, expressed by bacteria, or in solution for biological testing (Lam et al., 1991, Nature 354:82; Parmley et al., 1988, Gene 73:305; Scott and Smith, 1990, Science 249:386; Cwirla et al., 1990, Proc. Natl. Acad. Sci. U.S.A. 87:6378; Devlin et al., 1990, Science 249:404; Houghten et al., 1991, Nature 354:84; Fodor et al., 1991, Science 251:767; and Furka et al., 1991, Int. J. Peptide Protein Res. 37:487). Evaluation of peptides selected from such libraries requires rapid and efficient methods of peptide sequencing on the picomole level. Presently, Edman degradation (Niall, 1973, Methods Ezymol. 27:942) is the only widely used practical method for the direct determination of the amino acid sequence of polypeptides. However, in the past few years mass spectrometry has been proven to be a powerful and sensitive tool for peptide sequencing and is becoming a more and more useful alternative or complementary approach (Carr et al., 1991, Anal. Chem. 63:2801; Papayannopoulos and Biemann, 1992, Peptide Res. 5:83). Generation of mass spectra which contain necessary information for sequencing is not difficult and typical fragmentation pathways both for fast atom bombardment (FAB) and electrospray (ESI) collissionally induced dissociation have been characterized (Roepstorff and Fohlman, 1984, Biomed. Mass Spectrom. 11:601; Biemann, 1988, Biomed. Environ. Mass. Spectrom. 16:99). But sequence determination of an unknown peptide from mass spectral data is still a difficult task due to the huge number of possible sequences consistent with molecular weight (MW) of peptide, from which the correct one must be chosen by using spectral information about fragment ions and additional data (if any) about the peptide.

The recent advances in peptide synthesis discussed above allow generation of libraries of thousands to millions of peptide sequences. One advantage of such libraries is that non-natural amino acids can be incorporated in the peptide sequence. Such non-natural amino acids may not be amenable to Edman degradation. Thus, sequence determination of such peptides proceeds most readily by mass spectrometric methods. However, the present state of peptide sequencing by mass spectrometry remains imperfect.

There are two main approaches in sequence elucidation of peptides using mass spectrometry: (1) generation of all possible sequences consistent with the molecular weight of the peptide as the first step, with subsequent removal of those which are not consistent with experimental fragment ions (Matsuo et al., 1981, Biomed. Mass Spectrom, 8:139; Sakurai et al., 1984, Biomed. Mass Spectrom, 11:396; Hamm et al., 1986, Computer Appl. Biosci. 2:115); and (2) generation of all possible two to three membered subsequences and extension of these subsequences by one or more amino acids, either from the N- or C-terminus, such that only those subsequences which account for the greatest number of observed fragment ions are saved on every step (Ishikawa and Niwa, 1986, Biomed. Environ. Mass Spectrom. 13:373; Siegel and Bauman, 1988, Biomed. Environ. Mass Spectrom, 15:333; Johnson and Biemann, 1988, Biomed. Environ. Mass Spectrom 18:945; Bartels, 1990, Biomed. Environ. Mass Spectrom. 19:363; Scoble et al., 1987, Fresenius' Z. Anal. Chem. 327:239; Yates et al., 1991, Techniques in Protein Chem. 2:477; and Zidarov et al., 1990, Biomed. Environ. Mass Spectrom. 19:13). In the first approach, invalid sequences are removed on the final step of analysis, whereas the second approach uses spectral information to limit the number of possible subsequences on every step. In both cases deduction of the amino acid sequence becomes easier if additional information about the peptide is available. Thus, as discussed by Matsuo et al., supra, information concerning the kind and number of amino acids decreases dramatically the number of compositions, and sometimes a unique composition can be found. A correct answer for the sequence was obtained in each case when amino acid composition was used as an input data in an algorithm of Ishikawa and Niwa (1986, Biomed. Environ. Mass Spectrom. 15:333). Unfortunately, a combination of mass spectrometry with other techniques such as amino acid analysis, chemical derivatization, etc., is time consuming. Moreover, these analytic methods become very difficult when analysis must be carried out on picomoles of peptide.

It is an object of the present invention to provide a method for eliminating candidate peptide amino acid compositions or sequences elucidated by mass spectrometry by eliminating sequences that do not contain an observed number of exchangeable protons.

It is another object of the present invention to provide a method for using hydrogen-deuterium exchange to reduce the number of amino acid composition or sequence possibilities of a peptide of a particular mass.

It is a further object of the invention to provide a method for determining the composition or sequence of a peptide. Yet another object of the invention is to provide a method for sequencing a peptide that cannot be sequenced by Edman degradation.

SUMMARY OF THE INVENTION

The present invention is directed to methods for determining the amino acid composition, and more preferably, the sequence of a peptide using mass spectrometric techniques.

In one embodiment, the method for determining the amino acid composition or sequence of a peptide comprises determining the difference of the mass of the peptide from the mass of a derivative of the peptide, preferably a deuterium-hydrogen exchanged peptide, and from this difference determining the number of reactive moieties, e.g., exchangeable (labile) hydrogen atoms (protons). Candidate peptides having structures or sequences that do not contain the observed number of reactive moieties, e.g., exchangeable protons, are eliminated. Thus the number of possible amino acid compositions or sequences corresponding to a peptide of known molecular weight are reduced to a more manageable level. Furthermore, by determining the mass of a different derivative of the peptide, even more possibilities can be eliminated. Fewer candidates will need to be compared to observed data to determine the amino acid composition or sequence of the peptide. Moreover, the present invention provides a method for simplifying analysis by eliminating composition possibilities of a molecular ion peak of a peptide.

Suitable derivatives of the peptide include but are not limited to hydrogen-deuterium exchanged peptide and acylated peptide. Other derivatives are possible. To provide useful structural information, the derivative must result from quantitative reaction at one or more specific, predictable functional groups, e.g., amino, carboxyl, sulfhydryl, etc. In a preferred aspect, the derivative of the peptide is hydrogen-deuterium exchanged peptide. Hydrogen-deuterium exchange can proceed quantitatively in a small volume without subsequent purification. Exchange of all labile protons can occur.

In yet another embodiment of the invention, the sequence of a peptide selected from a library of synthetic peptides of known length can be determined by synthesizing a library of peptides, and terminating the synthesis of a portion of the peptides after a coupling step. This yields truncated fragments of the peptide. The molecular weight of the peptide and of the fragment are determined. The molecular weights of the fragment and the peptide and their fragmentation patterns are used to further limiting the structural possibilities. The molecular weight of the fragment can also be used to check the assignment of the fragmentation ions of the peptide.

In a further embodiment, the sequence of a peptide can be determined by determining the possible amino acid compositions of the peptide as described above, and calculating the possible composition fragments for of such compositions. The calculated fragments are compared with fragments observed experimentally, and the amino acid sequence is determined from this comparison.

In a further embodiment, the deuterium-exchanged acylated or otherwise derivatized peptide is fragmented. Information about the number of exchangeable protons or other reactive moieties in a fragment, which is available from comparison of daughter spectra of the peptide with daughter spectra of the deuterium exchanged or otherwise derivatized peptide, facilitates assignment of fragment ions.

In another embodiment, synthesis of a portion of the peptides in a library of peptides is terminated after each coupling step, whereby a set of sequentially truncated fragments of each peptide is formed. This set of sequentially truncated peptides is termed herein a "tag." The molecular weight of the truncated fragments of the peptide and the peptide are determined. The difference in the molecular weight of the peptide with the next smaller fragment, and each fragment with the next smaller fragment, corresponds to the molecular weight of an amino acid residue in the sequence of the larger fragment. Thus the sequence of the peptide can be determined by determining the difference in the molecular weight between each peptide or fragment thereof and the sequentially smaller fragment of the peptide.

In yet a further embodiment, the peptide and fragment or fragments thereof are derivatized. The molecular weights of the derivatives are determined and compared to the molecular weights of the peptide or fragments thereof before derivatization. These data can provide specific information about amino acids, such as lysine and glutamine, of identical molecular weight, which would not be distinguished by comparison of molecular weights of the truncated fragments alone.

In a further embodiment, the peptide to be sequenced is cleaved chemically or enzymatically, and a portion of the resulting fragments are derivatized. All of the fragments are analyzed. Information about the number of exchangeable or other reactive moieties in each of the fragments, which becomes available from a comparison of the mass spectra of the peptide fragments before and after derivatization, facilitates assignment of peaks in the mass spectrum of the peptide.

The methods of the present invention provide a preferred method for determining the amino acid composition or sequence of a peptide from a library of peptides of known size. A preferred embodiment of such a library is described in International Patent Publication WO 92/0091, published Jan. 9, 1992, entitled "Random Bio-oligomer Library, A Method Of Synthesis Thereof, And A Method Of Use Thereof" and in U.S. patent applications Ser. No. 07/546,845, filed Jul. 2, 1990, and Ser. No. 07/717,454, filed Jun. 19, 1991.

The present methods can be used to determine the amino acid composition or sequence of a peptide or fragment thereof that is isolated from a library of peptides attached to solid phase support used for their synthesis and subsequently cleaved from the solid phase support prior to mass spectroscopy analysis. In another embodiment, the peptide or fragment thereof can be in solution.

Thus a particular advantage of the present invention is that any algorithm used for elucidation of peptide sequence from mass spectrometry can be used more efficiently by excluding candidates that lack the observed number of exchangeable hydrogen atoms.

A further advantage is that a possible amino acid composition peptide can be determined by hydrogen-deuterium exchange to form a derivative of the peptide. Information about derivatives of the peptide allows elimination of a large number of possible peptide compositions of a given molecular weight. Once a large number of possible compositions have been eliminated, fragmentation analysis is more straightforward, since there are fewer possible patterns to compare with the observed fragmentation pattern.

Yet another advantage of the present invention is that it provides a powerful method for determining amino acid composition or sequence of a peptide selected from a library of peptides which contain a "tag" of sequentially truncated peptides.

Still another advantage of the invention is the ability to determine the sequence of a peptide that is not amenable to Edman degradation sequencing.

DETAILED DESCRIPTION OF THE INVENTION

Figure 1A:
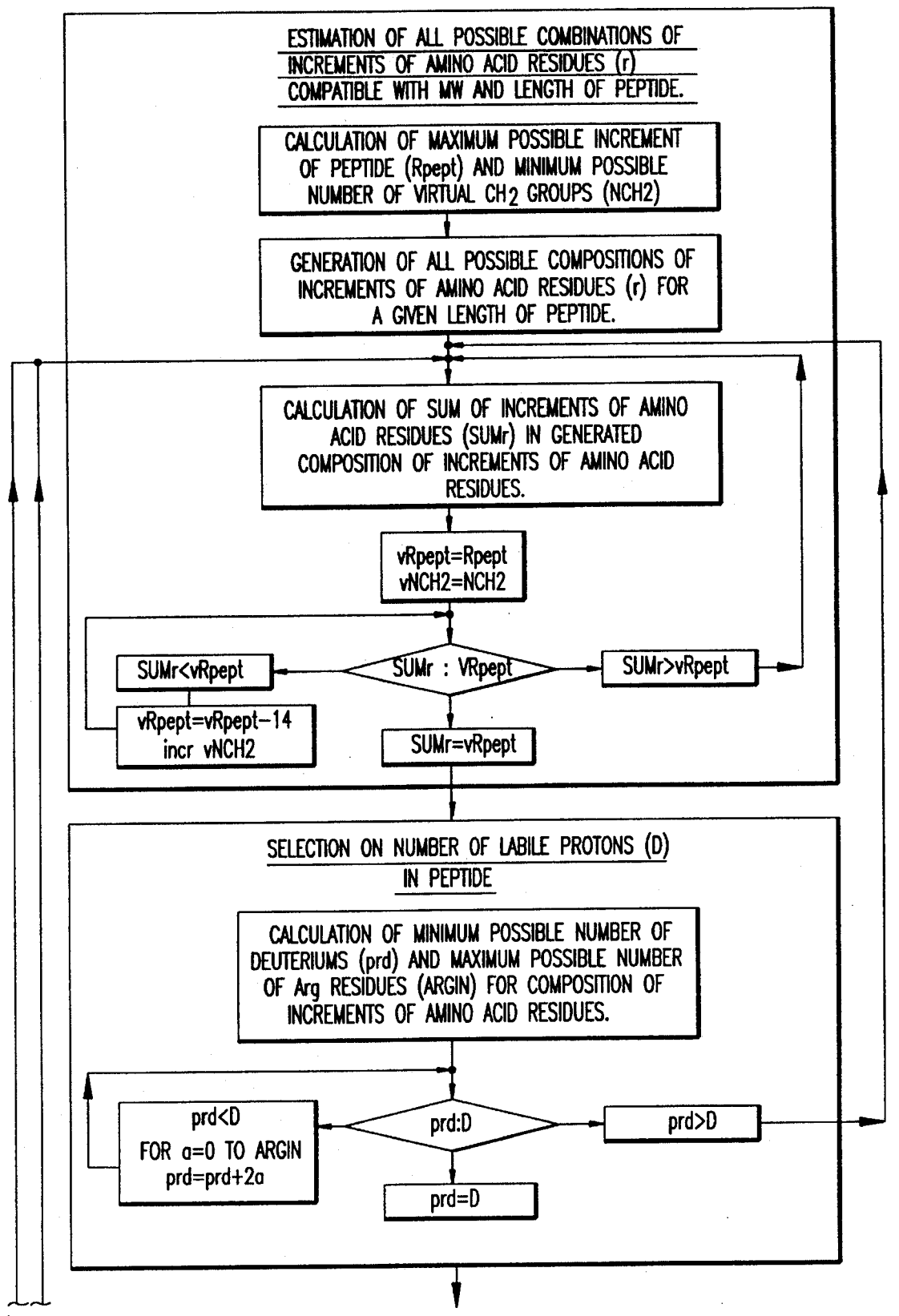
FIGS. 1A–B. Flow diagram of an algorithm for analyzing mass spectra of a peptide and a deuterium exchanged derivative of the peptide for possible amino acid compositions. The possible compositions can be used to more efficiently determine sequences.

The present invention is directed to methods for determining an amino acid composition, or more preferably, the sequence of a peptide using mass spectrometry. In one embodiment the molecular weight of a derivative of the peptide is determined using mass spectrometry. The difference between the molecular weight of the derivative and the molecular weight of the peptide depends on the number of reactive moieties on the peptide. Possible structures or sequences in the peptide capable of reacting with the derivatizing agent used. Possible sequences, that do not contain the observed number of reactive derivatizable moieties in the peptide, can thus be eliminated.

As used herein, the term "reactive moiety" refers to a functional group on the peptide that is amenable to quantitative derivatization or isotope exchange. The invention contemplates derivatization of small (less than 100 pmole) samples of peptide. Preferably, the derivatization or isotope exchange occurs under mild conditions and without a requirement for subsequent purification to avoid losing this small amount of material. Examples of reactive moieties include but are not limited to labile hydrogen atoms, which can be exchanged with deuterium atoms, and amines, which can be acylated. Other peptide derivatives can be prepared by selective esterification of free carboxyl groups, reaction of the guanido group of arginine with 9,10-phenanthroquinone, selective bromination or iodination of tyrosine, tryptophan, cysteine and methionine, derivatization of amino groups with reagents like phenylisothiocyanate and pthaldialdehyde, and alkylation of cysteine by bromo or iodo acetic acid or their derivatives. Cysteines or methionines oxidized by bromine or iodine can be reacted with water to form the sulfoxide derivatives of those amino acids. In the practice of the invention, substantially all possible reactive moieties must be reacted in forming a derivative of the peptide so that the mass spectrometric data can be used most meaningfully to eliminate various structural possibilities. According to the present invention, hydrogen-deuterium exchange is the preferred method for derivatization of a peptide, since, as pointed out infra, determination of the number of labile protons can eliminate numerous structural possibilities, deuterium exchange can be driven to completion, and the exchange reaction will proceed at microscopic scale.

It is possible to incompletely derivatize a peptide, so that not all of the possible reactive moieties are reacted. However, such an embodiment will in general not provide mass spectrometric data that are as useful.

In a further embodiment, the number of amino acid composition or sequence possibilities for a given peptide can be further reduced by comparing the molecular weight of a second derivative of a peptide to the molecular weight of the peptide, determining the number of reactive moieties in the peptide, and eliminating possibilities that do not account for the observed number of reactive moieties.

Knowledge of the number of amino acid residues in a peptide can further reduce the number of amino acid composition or sequence possibilities for the peptide. Peptides of a known number of residues can be obtained from peptide libraries. Preferably, such peptides are selected as disclosed in International Patent Publication WO 92/0091, published Jan. 9, 1992, entitled "Random Bio-oligomer Library, A Method Of Synthesis Thereof, And A Method Of Use Thereof" and in U.S. patent applications Ser. No. 07/546,845, filed Jul. 2, 1990, and Ser. No. 07/717,454, filed Jun. 19, 1991.

In another embodiment, a derivative that is a truncated fragment of the peptide can be prepared simultaneously with the peptide. Synthesis of a portion of the peptide can be terminated, so as to yield a truncated fragment of the peptide. The difference between the molecular weight of the peptide and the truncated fragment of the peptide corresponds to the molecular weight of the amino acid or peptide fragment that is present in the peptide but absent from the truncated fragment thereof. Moreover, the truncated fragment of the peptide, which is smaller and therefore less complex than the entire peptide, yields information about its structure. The truncated fragment of the peptide can also be used to check the assignments of fragment ions.

Once the possible composition or a number of possible compositions have been determined, fragmentation analysis can be used to help determine the sequence of the peptide. A reasonable number of fragmentation patterns based on the possible composition can be compared to the observed fragmentation pattern. The amino acid sequence of the peptide can be determined by matching the observed fragmentation pattern to the correct theoretical pattern of a possible sequence.

As used herein, the term "fragmentation pattern" refers to the pattern of ions of lower molecular weight than the peptide. Such ions are referred to as "daughter ions." Conditions for sample fragmentation are well known is mass spectroscopy. The fragments correspond to C-terminal fragments, N-terminal fragments, internal fragments and fragments that have lost side chains. Many computer programs and algorithms are available for analyzing mass spectra to determine peptide sequences (See, for example, Sakurai et al., 1984, Biomed. Mass Spectrom. 11:396; Biemann et al., 1988. Biomed. Environ. Mass Spectrom. 16:99). An advantage of one aspect of the present invention is that a small number of possible compositions are used to calculate probable fragmentation patterns, thus resulting in a manageable sequence determination problem. In another aspect, the present invention can be used to eliminate candidate sequences determined by any known algorithms (e.g., as described in Section 2, supra).

It should be understood that not all algorithms generate all possible sequences for comparison with experimental spectra. Most widely used algorithms (e.g., Ishikawa and Niwa, Biomed. Environ. Mass Spectrom. 13:373; Siegel and Baumann, 1988, Biomed. Environ. Mass Spectrom. 15:333; Johnson and Biemann, 1988, Biomed. Environ. Mass Spectrom. 18:945; Bartelo, 1990, Biomed. Environ. Mass Spectrom. 19:365; Scoble et al., 1987, Fresenius' Z. Anal. Chem. 327:239; Yates et al., 1991, Techniques in Prot. Chem. 2:477; and Zidarov et al., 1990, Biomed. Environ. Mass Spectrom. 19:13) create sequences by a stepwise, iterative process using two to three residue subsequences, and they do not necessarily generate all possible sequences consistent with MW. Even for such "iterative" algorithms, information about a limited number of amino acid compositions available from experiments with deuterium and other derivatized peptides, or sequentially truncated peptides, increases the accuracy of the approach. The present invention provides additional information about a peptide being studied, and this information can be either inserted in any algorithm or used to eliminate candidate sequences determined by any algorithm on the last stage of analysis.

In yet another embodiment of the invention for use with peptides selected from libraries such as those described in International Patent Publication WO 92/0091, sequentially truncated fragments of a peptide can be prepared simultaneously with the synthesis of the peptide itself. The sequentially truncated fragments of the peptide are formed by terminating the synthesis of a portion of the peptide after each coupling step. The difference in the molecular weight of the peptide or truncated fragment thereof and the next smaller truncated fragment of the peptide corresponds to the molecular weight of an amino acid. Thus the amino acid sequence can be determined.

The present invention can be used to determine the amino acid composition or the sequence of a peptide isolated from a natural or engineered source or prepared synthetically. More preferably, the present invention provides for sequencing a peptide isolated from a library of peptides. In a preferred aspect of the invention, the sequence of peptides isolated from a library described in International Patent Publication WO 92/00091, published Jan. 9, 1992 and in U.S. applications Ser. No. 07/546,845, filed Jul. 2, 1990 and Ser. No. 07/717,454, filed Jun. 19, 1991, are determined.

The term "peptide" is used herein in its broadest sense to refer to a compound of two or more subunit amino acids, amino acid analogs or peptidomimetics. The subunits may be linked by peptide bonds. In another embodiment, the subunits may be linked by other bonds, e.g., ester, ether, etc. As used herein the term "amino acid" refers to either natural and/or unnatural or synthetic amino acids, including glycine and both D or L optical isomers, and amino acid analogs and peptidomimetics. Peptide can also include various "designer" amino acids (e.g., β-methyl amino acids, α-methyl amino acids, $N^{\alpha}$-methyl amino acids, etc.). A peptide of three or more amino acids is commonly called an oligopeptide if the peptide chain is short. If the peptide chain is long, the peptide is commonly called a polypeptide or a protein.

In an additional embodiment, pyroglutamate may be included as the N-terminal residue of a peptide isolated from a library prepared synthetically. Pyroglutamate is not amenable to sequence by Edman degradation, thus the mass spectroscopic sequencing methods of the invention provide for determining the sequence of a peptide that contains pyroglutamate.

In a further embodiment, amino acids that confer useful chemical and structural properties can be chosen for inclusion in peptides of synthetic libraries. For example, peptides comprising D-amino acids will be resistant to L-amino acid-specific proteases in vivo. In addition, the present invention envisions sequencing peptides that have well defined structural properties, and the use of peptidomimetics, and peptidomimetic bonds, such as ester bonds, to prepare peptides that are not amenable to Edman degradation. In another embodiment, a peptide library may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such a peptide can demonstrate unique function and activity, such as extended half-lives in vivo due to resistance to metabolic breakdown, or protease activity.

The following non-classical amino acids may be incorporated in the peptides of a library that is prepared synthetically in order to introduce particular conformational motifs, and the present invention provides for determining the sequence of peptides containing such amino acids: 1,2,3,4-tetrahydroisoquinoline- 3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea).

The following amino acid analogs and peptidomimetics may be incorporated to induce or favor specific secondary structures: LL-Acp (LL-3-amino- 2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436.

The present invention further provides for sequencing of modified or derivatized peptides. Modifications of peptides are well known to one of ordinary skill, and include phosphorylation, carboxymethylation, and acylation. Modifications may be effected by chemical or enzymatic means. According to the present invention, such derivatization can be used to reduce the number of structural possibilities, thus simplifying further the problem of sequence determination.

In another aspect, glycosylated or fatty acylated peptide derivatives may be prepared and characterized by mass spectrometry. Preparation of glycosylated or fatty acylated peptides is well known in the art as exemplified by the following references;

1. Garg and Jeanloz, 1985, in Advances in Carbohydrate Chemistry and Biochemistry, Vol. 43, Academic Press.
2. Kunz, 1987, in Angew. Chem. Int. Ed. English 26:294–308.

3. Horvat et al., 1988, Int. J. Pept. Protein Res. 31:499–507.
4. Bardaji et al., 1990, Angew. Chem. Int. Ed. English, 23:231.
5. Toth et al., 1990, in Peptides: Chemistry, Structure and Biology, Rivier and Marshal, eds., ESCOM Publ., Leiden, pp. 1078–1079.
6. Torres et al., 1989, Experientia 45:574–576.
7. Torres et al., 1989, EMBO J. 8:2925–2932.
8. Hordever and Musiol, 1990, in Peptides: Chemistry, Structure and Biology, loc. cit., pp. 811–812.
9. zee-Cheng and Olson, 1989, Biochem. Biophys. Res. Commun. 94:1128–1132.
10. Marki et al., 1977, Helv. Chem. Acta., 60:807.
11. Fujii et al. 1987, J. Chem. Soc. Chem. Commun., pp. 163–164.
12. Ponsati et al., 1990, Peptides 1990, Giralt and Andreu, eds., ESCOM Publ., pp. 238–240.
13. Fujii et al., 1987, 1988, Peptides: Chemistry and Biology, Marshall, ed., ESCOM Publ., Leiden, pp. 217–219.

There are two major classes of peptide-carbohydrate linkages. First, ether bonds join the serine or threonine hydroxyl to a hydroxyl of the sugar. Second, amide bonds join glutamate or aspartate carboxyl groups to an amino group on the sugar. In particular, references 1 and 2, supra, teach methods of preparing peptide-carbohydrate ethers and amides. Acetal and ketal bonds may also bind carbohydrate to peptide.

Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in peptides of the library. This and other peptide-fatty acid conjugates suitable for use in peptides are disclosed in U.K. Patent GB-8809162.4, International Patent Application PCT/AU89/00166, and reference 5, supra.

Methods for the analysis of peptides by mass spectrometry are well known (see, e.g., the review by Carr et al., 1991, Anal. Chem. 63:2802–2824). Ionization methods include fast ion bombardment (FAB), electrospray (ESI), chemical induction decay (CID), matrix assisted laser desorption and plasma desorption. Preferred ionization methods are FAB, ESI and matrix assisted laser desorption.

For deuterium exchanged peptides, it will be readily apparent to one of ordinary skill that to avoid re-exchange, a deuterated sample matrix must be used. Preferred examples are $D_2O$, $CD_3OD$ or 50% $D_2O/CD_3OD$ for ESI and deuterated glycerol for FAB. Other suitable matrices known in the art can also be used.

PEPTIDE DERIVATIVES: DEUTERIUM EXCHANGED PEPTIDES

In a preferred embodiment, information about the number of labile protons (i.e. —OH, —NH, —$NH_2$, —SH and COOH— groups) in a molecule of peptide can be used for structure or sequence determination by mass spectrometry. As used herein the terms "exchangeable" and "labile" refer to the ability of a hydrogen ion in a solvent to replace a hydrogen ion on a peptide. In small and moderate size peptides (molecular weight less than 2000 Daltons), all labile hydrogen atoms are readily accessible to the solvents and rapid hydrogen/deuterium exchange occurs when such peptides are dissolved in deuterated solvents containing labile protons such as $D_2O$, $CD_3OD$, deuterated glycerol etc. (See Wuthrich, 1987, NMR of Proteins and Nucleic Acids, Wiley-Interscience, New York). Mixtures of deuterated solvents, such as 50% $D_2O/CD_3OD$ can also be used. Deuterated solvents of 99% or greater deuterium content are available commercially from many sources, for example, Sigma and Aldrich.

Measurement of mass difference between intact peptide and peptide after hydrogen-deuterium exchange gives the number of labile protons in the peptide molecule. As is well known in the art of mass spectrometry, the observed molecular weight of an ion corresponds to the mass of the molecule plus, usually, hydrogen (H). Under some conditions, the ion mass can include the mass of sodium (Na). Where the mass of a deuterium exchanged peptide ion is measured, the deuterium ion mass (D) will be included. Thus, the observed mass should be corrected by subtracting the mass of H, D, Na, etc.

Some technical difficulties connected with possible reexchange can be overcome with the help of the method described Katta and Chait (1991, Rapid Comm. Mass Spectrom. 5:214). Specifically, use of electrospray in an enclosed environment with dry air prevent introduction of water. Generally, if the ion source is completely isolated, water or other molecules containing protons can be excluded. Determination of number of labile protons can be performed with high accuracy.

The data in Table 1 report, inter alia, the number of labile (exchangeable) protons for each of the twenty natural amino acids when found in a peptide. This table applies to the D- as well as L-forms of these amino acids. Comparable data for other amino acids, such as described above, can be readily determined by one of ordinary skill in the art.

TABLE 1

Increments, number of virtual $CH_2$ groups and number of exchangeable protons of amino acid residues

| Amino acid residue | G | A | V | L I | N | K Q | R | S | T | D | E | W | M | C | F | Y | H | P |
|---|---|---|---|---|---|---|---|---|---|---|---|---|---|---|---|---|---|---|
| Increment | 0 | 0 | 0 | 0 | 1 | 1 | 1 | 2 | 2 | 2 | 2 | 3 | 4 | 4 | 6 | 8 | 10 | 12 |
| Number of $CH_2$ groups | 0 | 1 | 3 | 4 | 4 | 5 | 7 | 2 | 3 | 4 | 5 | 9 | 5 | 3 | 6 | 7 | 5 | 2 |
| Number of labile protons | 1 | 1 | 1 | 1 | 3 | 3 | 5 | 2 | 2 | 2 | 2 | 2 | 1 | 2 | 1 | 2 | 2 | 0 |

The experimental data obtained by mass spectrometric analysis of peptides that have undergone hydrogen-deuterium exchange can be used to exclude possible sequences that are not consistent with data about the number of labile protons. As shown in an Example in Section 6, infra, information about the number of exchangeable protons can exclude 50% of the possible sequences determined by detailed analysis of fragmentation pattern alone. In another Example in Section 6, thirteen of twenty high-scoring probable sequences could be excluded.

It should be noted that removal of noncorrect sequences on the last stage of analysis can be applied to any algorithm for sequencing peptides that does not require composition of the peptide as an input.

Another embodiment of the present approach is to reduce the number of compositions consistent with MW of peptide in order to facilitate subsequent analysis of peptide structure. To demonstrate efficiency of this approach, an algorithm for calculating compositions compatible with molecular weight and number of exchangeable protons in a molecule has been developed. This algorithm was developed specially for the purpose of analysis of peptide libraries (See International Patent Publication WO 92/00091, Jan. 9, 1992). All possible combinations of peptides with fixed length are generated in the course of library synthesis, and the algorithm of the present invention uses information available from the synthesis protocol about the number of amino acid residues (n) and experimental data about molecular weight of the peptide (MW) and number of exchangeable protons (D). One of possible way to evaluate all combinations of amino acids compatible with MW, n and D is to generate at first all possible compositions with length n and then to choose among them those which fit experimental data about MW and finally, among the latter, those which fit number of labile protons. But the huge amount of all possible compositions for a peptide of given length makes this way time-consuming. For example, for a decapeptide the number of possible sequences equals 16,777,220.

To avoid this difficulty, the present invention provides an algorithm that divides the twenty natural amino acids into several groups, termed herein "incremental residues," and creates at first compositions of these incremental residues rather than twenty amino acids. Compositions of incremental residues are termed herein "incremental compositions." Then the algorithm can be used to preliminarily select among incremental compositions. The algorithm then converts the incremental compositions into compositions of amino acids, from which a final selection is made. A flow chart of a preferred algorithm is provided in FIGS. 1A–B.

Generally the chemical structure of amino acid residue is (—NH—CHR—CO—), where for aliphatic amino acids (Gly, Ala, Val, Leu, Ile), R=alkyl; for acidic residues (Asp, Glu), $R=(CH_2)_k—CO_2HCOOH$, etc. Thus, the molecular weight of an amino acid residue can be represented as the sum of the molecular weight of the constant part (—NH—CH$_2$—CO—) and the molecular weight of several CH$_2$ groups (k) and some increment (r). The number of several CH$_2$ groups (k) and the increment (r) can be calculated in the following way: the value 14 (MW of CH$_2$ group) is subtracted from the remainder of the subtraction of MW of the constant part from MW of the residue until the remainder is less than 14. Thus the number of times we subtract 14 (k) is equal to a number of CH$_2$ groups which are termed herein "virtual CH$_2$ groups", and the remainder (less than 14) is termed the increment (r). It should be noted that the number of virtual CH$_2$ groups obtained in the result of calculation coincide with real CH$_2$ groups in the structure of an amino acid residue only for aliphatic residues; hence the use of the term virtual CH$_2$ groups to describe the value "k". Thus every residue is characterized by a number of virtual CH$_2$ groups (k) and the increment (r), and twenty amino acids can be divided into nine groups with equal increments within every group (Table 1). Since the twenty natural amino acids form only nine groups of increments, the number of all possible compositions of increments is much less than the number of compositions of amino acids. For example for decapeptide it is only 43,758 (rather than 16,777,220), and all possible compositions of increments for a given length of peptide can be easily generated.

Similar procedure of the calculation of number of virtual CH$_2$ groups (K) and increment (R) can be done for peptide with known MW, number of residues and C-and N-terminal groups. (Note that the number of virtual CH$_2$ groups and increment are designated k and r, respectively, for an amino acid residue, and K and R, respectively, for a peptide.) Obviously the sum of increments of substituent amino acid residues is either equal to the increment of peptide R or more than R by 14, 28, 42, etc. However, the sum of increments (r) does not exceed 12 multiplied by n (12 is the maximum increment, i.e. increment of a proline residue [see Table 1], and n is the number of residues in the peptide). Thus for preliminary selection among all possible compositions of increments generated, one must compare the sum of increments in every composition (SUMr) with the increment of peptide R and with values R+14, R+28, R+42, etc., selecting for subsequent analysis only those compositions of increments in which SUMr coincides with R or R+14, or R+28 or R+42, etc.

In order to obtain amino acid compositions of peptides for a given MW, it is necessary to convert the obtained compositions of incremental residues into compositions of amino acids. This is not a difficult task since only from one to four amino acids correspond to every increment (see Table 1). One can make a final selection using either molecular weights of amino acid residues or calculated number of virtual CH$_2$ groups. Such two step evaluation of compositions of peptides for a given MW using preliminary arrangement of amino acids in groups enables considerable savings of calculation time.

Selection based on the number of exchangeable protons can be done on the last step of analysis, choosing among amino acid compositions consistent with a molecular weight of the deuterium-exchanged derivative those that fit the number of exchangeable protons. But as it is clear from Table 1, residues with increments 0,4,6, have only one or two (for Cys) exchangeable protons; residues with increment of 12 have no exchangeable protons at all; residues with increments of 2,3,8,10 have two labile hydrogens; and residues with increments of 1 have three or five (for Arg) exchangeable protons. This relationship between the value of the increment of a residue and the number of labile hydrogens enables one to select incremental compositions based on the number of exchangeable protons in the peptide determined experimentally, i.e., reduce the number of possible incremental compositions.

Once an amino acid composition or a set of probable amino acid compositions for a peptide has been determined, the sequence or a set of probable sequences for the peptide may be determined. One approach for sequence determination involves generating all possible sequences for each of the amino acid composition assignments for the peptide of interest and comparing the calculated fragmentation pattern for each of these sequences with the fragmentation pattern from the mass spectrum of the peptide. However, this procedure is time consuming. A preferred alternative approach involves calculation of all possible composition fragments for each of the amino acid compositions assigned to the peptide of interest followed by selection of calculated fragments that match fragments in the mass spectrum of the peptide, use of these selected fragments in determining partial sequences for the peptide, and use of the partial sequences in proposing a full sequence for the peptide. The following algorithm is used in this preferred sequencing approach.

(1) Calculate all possible fragments consistent with each of the amino acid compositions under consideration for the peptide to be sequenced. It is important to note that a fragment may be N-terminal or C-terminal, which must be accounted in the calculation.

(2) Evaluate fragments calculated in Step (1) as N-terminal fragments. This requires adding (or substracting) appropriate offsets (see Bartels, 1990, Biomed. Env. Mass Spectr. 19:363–368) to the molecular weight of the constitutive residues of the fragment to account for different fragmentation patterns. Fragmentation will likely occur at one of three positions depending on the method of fragmentation: the Co—CO bond; the peptide bond; or the N—C$\alpha$ bond, and offsets for each possibility can be included in the calculation. Although any fragmentation technique can be used, in a preferred aspect, electrospray low energy collision induced dissociation (CID) is used to form fragment ions. This method usually results in a single cleavage event, thus limiting the complexity of the mass spectrum. The usual offset calculations for N-terminal fragments in electrospray low energy CID are A series (fragment MW-28); A-17 series (fragment MW-45 [28+17]); B series (fragment MW); and B-17 series (fragment MW-17).

(3) Select all N-terminal fragments from the set of calculated fragments evaluated as N-terminal fragments that match a daughter ion peak found in the mass spectrum of the peptide.

(4) Evaluate the fragments calculated in Step (1) as C-terminal fragments, which also requires adding (or substracting) appropriate offsets to the molecular weight of the constitutive residues of the fragment. For the preferred electrospray low energy CID method, the usual offset calculations are the Y" series (fragment MW+2) and the Y"-17 series (fragment MW-15) [2-17]).

(5) Select all C-terminal fragments from the set of calculated fragments evaluated as C-terminal fragments that match a daughter ion peak found in the mass spectrum of the peptide.

(6) Reexpress C-terminal fragments selected in Step 5 by deducing the composition of N-terminal fragments complementary to the C-terminal fragment. Complementary fragments are those that contain an amino acid composition that, combined with the observed fragment, corresponds to the composition of the peptide under consideration. By starting with the smallest C-terminal fragment, and "inserting" this into the next larger fragment, a sequence or partial sequence for the peptide under consideration is determined. It can be readily appreciated that comparison of molecular weight differences between selected composition fragments that differ in the number of amino acids by one yields preliminary sequence information, since the molecular weight difference corresponds to the additional amino acid at the position. For example, an amino acid corresponding to the molecular weight difference between a tetramer fragment and a trimer fragment is the amino acid at the fourth position of the peptide under consideration.

Every candidate sequence generated using the algorithm above receives a score, the highest score corresponding to the most probable sequence. One way to score a sequence candidate is to add the number of calculated fragments which can be matched with fragments found in the mass spectrum of the peptide. In a further embodiment, candidate sequence scores can also include a value of one-half of the number of immonium ions (See Biemann, 1990, Meth. Enzymol. 193: 455) derived from single amino acids in the mass spectrum of the peptide which are matched by the calculated fragments.

Information about the number of exchangeable protons discussed above can be applied not only to a peptide but also to its fragment ions. One of the main difficulties that arises in sequencing an unknown peptide is the fact that combinations of some amino acid residues have the same nominal mass as a single larger residue or a different combination, for example: -Ala,Gly- and Gln or Lys; -Gly,Gly- and -Asn-; -Gly,Val- and -Arg-; -Ala,Asp- and -Trp-; -Ser,Val- and -Trp-; -Gly,Leu- and -Ala,Val-, etc. Such combinations of amino acids usually hinder correct assignment of fragment ions and can lead to ambiguous results in sequencing of unknown peptides. For example Siegel and Bauman (1988, Biomed. Environ. Mass Spectrom. 15:333) pointed out that although the sequence of one peptide contained -Ala-Gly-, the output of computer analysis of this peptide with their algorithm gave -Gln- instead of -Ala-Gly-. Similar problems in sequencing of unknown peptides are described in Scoble et al. (1987, Fresnius' Z. Anal. Chem. 327:239), where -Trp- appeared in the determined sequence of the peptide, which actually contained -Val-Ser-. This kind of problem has been recognized as one of limitations of another approach to peptide sequencing (Yates et al., 1991, Techniques in Protein Chem. 2:477). Information about the number of exchangeable protons in fragment ions available from comparison of mass spectra of intact peptide and deuterated peptide enable unambiguous assignment of most of these fragment ions. For example -Ala,Gly- contains 2 labile protons rather than 3 in -Gln-; likewise 2 labile protons are found in Trp and 3 in -Val-Ser-, etc.

Thus, in a preferred aspect, hydrogen-deuterium exchange is used to first determine a composition or a sequence of the intact peptide using any of described algorithms, then analyze the fragmentation ion spectrum of the peptide after hydrogen-deuterium exchange. An attractive advantage of this hydrogen-deuterium exchange technique for sequencing peptides is to check if the assignment of fragment ions made by an algorithm is consistent with the number of exchangeable protons of the fragment. The determination of the number of exchangeable protons in the fragment ions(s) is made experimentally from comparison of daughter spectra of the peptide and of the deuterium exchanged peptide.

As described above, the present methods provide a preferred route for analysis of peptides isolated from a library of peptides. One major advantage of such peptides is that the number of amino acid residues in the peptide is known, thus eliminating one variable from the problem of determining the composition or sequence of a peptide. As can be seen in the Example Section 7, infra, the number of possible amino acid compositions of a peptide of a known number of amino acid residues and observed molecular weight is drastically reduced when the number of exchangeable protons is considered.

In another embodiment, the sequence of a peptide obtained from natural or engineered sources can be determined. The mass of the peptide and the deuterium exchanged peptide are determined and amino acid composition or sequence analysis is performed.

Additionally, proteins can be isolated, and analyzed according to the present methods. Mass spectrometric analysis of a protein generally requires digesting the protein into fragments enzymatically (e.g., with protease such as trypsin, chymotrypsin, papain, etc.) or chemically (e.g., with cyanogen bromide). Deuterium exchange, preferably in the presence of a protein denaturant such as urea (deuterated) or guanidinium-HCl (deuterated) to allow access for exchange of all protons, can precede cleavage of a protein. More preferably, however, the deuterium exchange proceeds after the cleavage reaction. Thus, every peptide is analyzed directly with its deuterium exchanged derivative. Preparing the deuterium exchanged peptides after cleavage of the protein also avoids problems that might occur from anomalous results from one cleavage reaction to the next.

OTHER PEPTIDE DERIVATIVES

As pointed out above, peptide derivatives can be prepared by well known reactions. Some of these derivatives include but are not limited to selective esterification of free carboxyl groups, reactions of the guanidino group of arginine with 9,10-phenanthroquinone, selective bromination or iodination, e.g., of the aromatic ring of tyrosine and tryptophan, derivatization of amino groups with reagents like phenylisothiocyanate and pthaldialdehyde, and alkylation of cysteine by bromo or iodo acetic acid or their derivatives.

In another embodiment, a fragment of the peptides in a library can be prepared by terminating synthesis of a portion of the peptides. Termination of synthesis can be achieved by reacting the peptide after N-terminal deprotection with an activated carboxylic acid that lacks an amino group, for example acetic acid, benzoic acid, etc. More preferably, the carboxylic acid contains a substitutent with a unique isotopic ratio. Such a substituent can serve as a marker in the mass spectrum for the peptide fragment, since a unique peak, such as a doublet, will be observed. Suitable isotopes for substitution include but are not limited to bromine, which has two naturally occurring isotopes of 78.9183 (50.69%) and 80.9163 (49.31%) molecular weight. (These are termed $Br^{79}$ and $Br^{81}$, respectively.) Thus a brominated molecular ion will consist of a doublet of two MW difference.

Analysis of mass spectra for peptide sequence determination proceeds along very much the same lines using other peptide derivatives as for deuterium exchanged derivatives. That is, the spectra of the peptide and the derivative of the peptide are compared. From this comparison the number of reactive moieties of the peptide can be determined. If candidate peptide sequences have been produced by analysis of mass spectra, e.g., by using a computer assisted algorithm to analyze fragmentation data, the information about the number of reactive moieties can be used to eliminate inconsistent possibilities.

For example, if the peptide derivative is acetylated, and incorporates two or more acetyl groups, candidate peptides must contain one or more amino groups in addition to the N-terminal amine. Thus candidates lacking lysine (which contains an ε-amino group) can be eliminated from a list of candidates determined from mass spec analysis.

Applying these basic principles, it becomes apparent that any derivative of a peptide can be used to evaluate the number of reactive moieties of a specific type in a peptide.

Similarly, the assignment of fragment ions can be checked by comparing daughter ion spectra of a peptide with the daughter ion spectra of the derivative of the peptide. Assignment of residues containing reactive moieties can be checked by comparing the fragment ion molecular weight with the molecular weight of the derivative fragment ion.

Similarly, composition tables, such as are shown in the Example in Section 7, infra, can be prepared for any derivative, since the number of possible combinations can be reduced by eliminating possibilities that are not Consistent with the experimental data.

A truncated fragment derivative of a peptide can also greatly increase the efficiency of sequence determination. First, the amino acid composition or sequence of the truncated fragment can be determined more easily since it is a smaller peptide of known length. Knowledge about any variable of the peptide greatly reduces the difficulty of sequence determination. Furthermore, the truncated peptide fragment can be used to verify the assignment of fragmentation ions, since the truncated fragment is of known size. Thus confusion between selection of a dipeptide or single amino acid of identical molecular weight is unambiguously resolved by the knowledge of whether there are one or two amino acid residues to account for.

It will be readily apparent that these techniques can be combined, and in combination, further reduce the number of variables in determining a peptide amino acid composition or sequence using mass spectrometry.

SEQUENTIALLY TRUNCATED PEPTIDES

The technology described in International Patent Publication WO 92/0091, published Jan. 9, 1992, entitled "Random Bio-Oligomer Library, A Method Of Synthesis Thereof, And A Method Of use Thereof" and in U.S. patent applications Ser. No. 07/546,845, filed Jul. 2, 1990, and Ser. No. 07/717,454, filed Jun. 19, 1991 is based on a determination of structure of peptide attached to one solid phase particle. Standard methods of sequencing peptides are based on the sequential degradation of a peptide. This is normally done by Edman degradation. Faster methods utilize mass spectrometry and fragmentation of a peptide molecule in a peptide backbone. However, as we described earlier, mass spectrometric techniques suffer from certain uncertainties in structure determinations. In building peptide libraries, the present invention contemplates a "tag" for every peptide by the whole history of its synthesis. This history can be read at the time of structure determinations.

In practice, the set of sequentially truncated fragments of the peptide is made in the following way. In every step of the synthesis a certain percentage (2–5%) of a peptide chain is terminated by a noncleavable group. In a specific embodiment, the noncleavable group is bromobenzoic acid. In this way the synthesized peptide is obtained in slightly lower yield, but it is accompanied on the same bead by all shorter fragments. By reading the differences in molecular weights of all these fragments the sequence of the peptide can be read. To simplify the reading, one can apply as the terminating group a group containing an atom with a unique isotopic ratio. As discussed above, a preferred marker atom is bromine, which can be introduced as bromoacyl or bromoaroyl group. A mixture of different groups for termination can also mark the peptide fragment.

Generally, the amino acids used for peptide synthesis are the base-labile $N^\alpha$-amino protected 9-fluorenylmethoxycarbonyl (Fmoc) amino acids first described by Carpino and Han (1972, J. Org. Chem. 37:3403–3409). The method of the present invention may also be used with the Boc-amino acids $N^\alpha$-t-butyloxycarbonyl). Both Fmoc and Boc $N^\alpha$-amino protected amino acids can be obtained from Fluka, Bachem, Advanced ChemTech, Sigma, Cambridge Research Biochemical or Peninsula Labs or other chemical companies familiar to those who practice this art. In addition, the method of the invention can be used with other $N^\alpha$-protecting groups that are familiar to those skilled in this art. The coupling of the amino acids may be accomplished by techniques familiar to those in the art and provided, for example, in Stewart and Young, 1984, Solid Phase Synthesis, Second Edition, Pierce Chemical Co., Rockford, Ill.; Fields and Noble, 1990, "Solid phase peptide synthesis utilizing 9-fluorenylmethoxycarbonyl amino acids", Int. J. Pept. Protein Res. 35:161–214.

Termination of peptide synthesis can be accomplished by means well known in the art, using standard synthetic methods. For example, a deprotected $N^\alpha$-amine can be reacted with acetic anhydride to block the amine group. Since acetic acid does not contain an amine group itself, no further addition of activated amino acids to that peptide is possible. Thus synthesis is terminated. As is readily apparent to one of ordinary skill in this art, many carboxylic acid groups can be used to terminate synthesis of a peptide. In addition to acetic acid, preferred blocking groups include but are not limited to bromoacetic acid, benzoic acid, and bromobenzoic acid.

EXAMPLE: SEQUENCE ANALYSIS WITH DEUTERIUM EXCHANGED PEPTIDES

The present Example demonstrates in a model system how determination of the number of labile protons in a peptide can eliminate candidate peptide sequences elucidated from mass spectrometric analysis. Furthermore this example demonstrates that, according to the present invention, by determining the number of labile protons, which can be obtained experimentally, the correct sequence can be selected from the highest scoring probable sequence having that number of labile protons.

According to the present invention, the most straightforward use of experimental data about the number of exchangeable protons is the following: to exclude those sequences obtained from an analysis of mass spectral data (using any algorithm) that are not consistent with the data about number of labile protons. Table 2 (SEQ. ID NOS: 6-25) presents results of analysis of an α-chymotryptic peptide (from Johnson and Biemann, 1988, Biomed. Environ. Mass Spectrom. 18:945). Twenty sequences have high scores calculated according to the reference, and these scores fall in a narrow range. This paper reports additional detailed analysis of every one of these sequences to choose a correct one. We have calculated the number of labile protons for each peptide candidate. The correct number of labile protons is 23, corresponding to peptide VNSQIQPGQVVVF (SEQ. ID NO: 6). This value would be determined experimentally. As is shown in Table 2, information about number of exchangeable protons excludes 11 of 20 sequences, thus saving computer time and increasing the accuracy of the result.

The results with another example from Johnson and Biemann, supra, are shown in Table 3 (SEQ. ID NOS: 26-45). Computer analysis of spectrum of fragment ions of this peptide yielded twenty most probable sequences with similar high score. The number of labile protons for each peptide candidate was determined. The correct number of labile protons, which can be determined experimentally, is 20, corresponding to peptide QQGQQVGEF (SEQ. ID NO: 36). As is clear from Table 3, the present invention provides an approach that would exclude 17 of the twenty choices. Moreover, the correct choice has the highest score among those candidate sequences that fit the observed number of exchangeable protons in the molecule.

In both experiments, information about labile protons in the peptide increase accuracy of sequence evaluation. In the second experiment, combination of hydrogen exchange with the algorithm used by Johnson and Biemann, supra, enables unambiguous sequence determination. It should be noted that removal of incorrect sequences on the last stage of analysis can be applied to any algorithm of sequencing peptides described in literature that does not need composition of a peptide as an input.

TABLE 2

Results of computer analysis of CID spectrum of α-chymotrypsin (from Johnson and Biemann, supra), and the calculation for every probable sequence of the number of labile protons. The correct sequence is underlined.

| SEQ. ID No.: | Score | Candidate sequences | Number of labile protons | Candidate sequences with the same number of labile protons as correct one |
|---|---|---|---|---|
| 6 | 0.898 | VNQIQPGQVVVF | 23 | VNQIQPGQVVVF |
| 7 | 0.870 | GGVSQIQPGQVVVF | 22 | |
| 8 | 0.870 | NVSQIQPGQVVVF | 23 | NVSQIQPGQVVVF |
| 9 | 0.867 | VSGGQIQPGQVVVF | 22 | |
| 10 | 0.864 | VNSXQQPGQVVVF | 22 | |
| 11 | 0.864 | GRSQIQPGQVVVF | 25 | |
| 12 | 0.862 | GGADQIQPGQVVVF | 22 | |
| 13 | 0.862 | XADQIQPGQVVVF | 21 | |
| 14 | 0.862 | NADQIQPGQVVVF | 23 | NADQIQPGQVVVF |
| 15 | 0.857 | GQDQIQPGQVVVF | 23 | GQDQIQPGQVVVF |

TABLE 2-continued

Results of computer analysis of CID spectrum of α-chymotrypsin (from Johnson and Biemann, supra), and the calculation for every probable sequence of the number of labile protons. The correct sequence is underlined.

| SEQ. ID No.: | Score | Candidate sequences | Number of labile protons | Candidate sequences with the same number of labile protons as correct one |
|---|---|---|---|---|
| 16 | 0.852 | SPDQIQPGQVVVF | 21 | |
| 17 | 0.850 | SVGGQIQPGQVVVF | 22 | |
| 18 | 0.845 | GGEGQIQPGQVVVF | 22 | |
| 19 | 0.845 | NEGQIQPGQVVVF | 23 | NEGQIQPGQVVVF |
| 20 | 0.842 | SRGQIQPGQVVVF | 25 | |
| 21 | 0.837 | VNSQIQPGQVTPF | 23 | VNSQIQPGQVTPF |
| 22 | 0.836 | GGVSXQQPGQVVF | 21 | |
| 23 | 0.836 | NVSXQQPGQVVVF | 23 | NVSXQQPGQVVVF |
| 24 | 0.835 | DQGQIQPGQVVVF | 23 | DQGQIQPGQVVVF |
| 25 | 0.835 | QDGQIQPGQVVVF | 23 | QDGQIQPGQVVVF |

TABLE 3

Results of computer analysis of CID spectrum of KKGQKVGEF SEQ. (ID NO: 46) (from Johnson and Biemann, supra) and the calculated numbers of labile protons in every possible sequence. The correct sequence is underlined.

| SEQ. ID No.: | Score | Candidate sequences | Number of labile protons | Candidate sequences with the same number of labile protons as correct one |
|---|---|---|---|---|
| 26 | 0.850 | GAQGAGQVGEF | 18 | |
| 27 | 0.850 | GAQGQAGVGEF | 18 | |
| 28 | 0.850 | GAQGQQVGEF | 19 | |
| 29 | 0.850 | GAQGQQGVEF | 19 | |
| 30 | 0.848 | AANGQQVGEF | 19 | |
| 31 | 0.840 | AGQGAGQVGEF | 18 | |
| 32 | 0.840 | AGQGQAGVGEF | 18 | |
| 33 | 0.840 | AGQGQQVGEF | 19 | |
| 34 | 0.840 | QQGAGQVGEF | 19 | |
| 35 | 0.840 | QQGQAGVGEF | 19 | |
| 36 | 0.840 | QQGQQVGEF | 20 | QQGQQVGEF |
| 37 | 0.834 | NAAGQQVFEG | 19 | |
| 38 | 0.832 | AGGAGQQVGEF | 18 | |
| 39 | 0.832 | GAGAGQQVGEF | 18 | |
| 40 | 0.832 | GAGAGQQGVEF | 18 | |
| 41 | 0.832 | QGAGQQVGEF | 19 | |
| 42 | 0.827 | AGQGQQGVEF | 19 | |
| 43 | 0.827 | QQGQQGVEF | 20 | QQGQQGVEF |
| 44 | 0.826 | AANGQQVWF | 18 | |
| 45 | 0.826 | QQGQANVEF | 20 | QQGQANVEF |

These results demonstrate the power of the present invention to select the correct peptide sequence from a set of candidate sequences elucidated by mass spectrometric analysis.

EXAMPLE: AMINO ACID COMPOSITION ANALYSIS WITH DEUTERIUM EXCHANGED PEPTIDES

This Example demonstrates in a model system how the experimental determination of the number of labile protons in a peptide of a known number of amino acids can assist amino acid composition analysis.

Figure 1B:
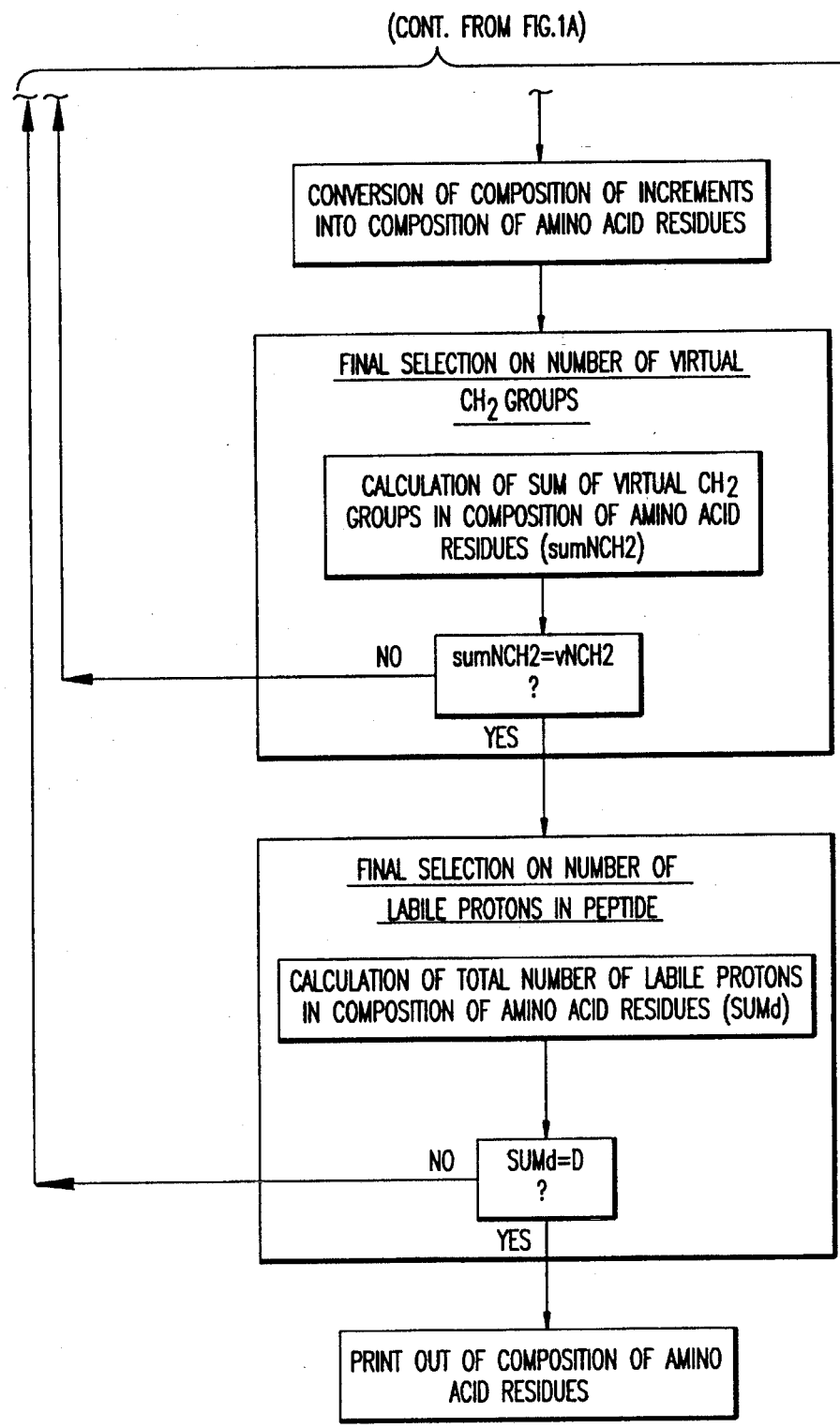

Results of the use of the algorithm described in FIGS. 1A–B and Section 5.1., supra, to calculate possible compositions of different peptides are represented in Table 4. The data in this table demonstrate that information about number of exchangeable protons reduces the number of possible compositions as much as ten-fold or greater.

TABLE 4

Composition analysis of peptides with known amino acid number.

| N | $n^1$ | MW | $A^2$ | $B^3$ | $D^4$ |
|---|---|---|---|---|---|
| 1 | 6 | 774 | 456 | 17 | 9 |
| 2 | 6 | 692 | 439 | 91 | 13 |
| 3 | 6 | 673 | 374 | 21 | 9 |
| 4 | 8 | 1045 | 3428 | 367 | 16 |
| 5 | 8 | 899 | 2988 | 502 | 15 |
| 6 | 5 | 573 | 144 | 4 | 8 |

[1] n — number of residues
[2] A — number of possible compositions without restriction on number of labile protons
[3] B — number of compositions consistent with number of labile protons
[4] D — number of exchangeable protons in molecule The examples in Table 4 clearly show that given three parameters—number of residues, molecular weight and the number of exchangeable protons—the number of composition possibilities decreases dramatically. Composition alone provides useful information about peptides isolated from a library. Furthermore, by restricting the number of theoretical compositions for fragmentation analysis, computation time for the analysis of a fragmentation spectrum is reduced significantly.

Table 5 reports the results of calculation using the algorithm described in Section 5.1, supra, for composition analysis of different peptides. The data in this table show the distribution of the number of compositions versus molecular weight and number of exchangeable protons in peptides of six-residues. These data demonstrate that information about the number of exchangeable protons reduces considerably the number of possible compositions of peptides of known length, and sometimes unique compositions can be obtained. It should be appreciated from Table 5 that for the total the value for the number of compositions having the specific molecular weight and number of exchangeable protons ranges up to at most about 25% of the total number of possible compositions at that value of molecular weight.

TABLE 5

Distribution of the number of possible compositions for a number of exchangeable protons (D) and MW for six-residue peptides.

| MW D[1] | 600 | 700 | 800 | 900 |
|---|---|---|---|---|
| 2 | 1 | — | — | — |
| 3 | — | — | — | — |
| 4 | — | 1 | — | — |
| 5 | 1 | 2 | — | — |
| 6 | 5 | 2 | 1 | — |
| 7 | 8 | 8 | 2 | — |
| 8 | 9 | 14 | 4 | 1 |
| 9 | 48 | 27 | 14 | 1 |
| 10 | 16 | 65 | 19 | 1 |
| 11 | 19 | 92 | 14 | 9 |
| 12 | 46 | 52 | 40 | 14 |
| 13 | 9 | 77 | 43 | 6 |
| 14 | 11 | 29 | 39 | 10 |
| 15 | — | 41 | 41 | 2 |
| 16 | 2 | 23 | 23 | 7 |
| 17 | — | 17 | 27 | 6 |
| 18 | — | 9 | 15 | 6 |
| 19 | — | — | 9 | — |
| 20 | — | 3 | 3 | 2 |
| 21 | — | — | 6 | — |
| 22 | — | — | 2 | 2 |
| 23 | — | — | 6 | 1 |
| 24 | — | — | 1 | 1 |
| 25 | — | — | 2 | 2 |
| 26 | — | — | — | 1 |
|  | $\Sigma^2 = 175$ | $\Sigma = 462$ | $\Sigma = 311$ | $\Sigma = 71$ |

[1]D — number of labile protons
[2]$\Sigma$ — total number of possible compositions of six residue peptide for a given MW

EXAMPLE: ELECTROSPRAY MASS SPECTRA OF PEPTIDES AND DEUTERIUM EXCHANGED DERIVATIVES THEREOF

This Example shows the ease with which one can measure the mass of a peptide and a deuterium exchanged derivative of the peptide. The deuterium exchange proceeds very easily in deuterated, protic solvent, such as $D_2O$, $CD_3OD$, etc.

MATERIALS AND METHODS

Peptides LAYWK-$NH_2$ (SEQ. ID NO: 1), WNYFK-$NH_2$ (SEQ. ID NO: 2) and KFWKT-$NH_2$ (SEQ. ID NO: 3) were prepared using standard techniques. Hydrogen-deuterium exchange was performed in 50% deuteriated water/deuterated methanol. Mass spectra were obtained on a Finnigan MAT TSQ-700 triple sector quadrupole mass spectrometer equipped with a standard Finnigan electrospray ion source.

RESULTS AND DISCUSSION

Figure 2A:
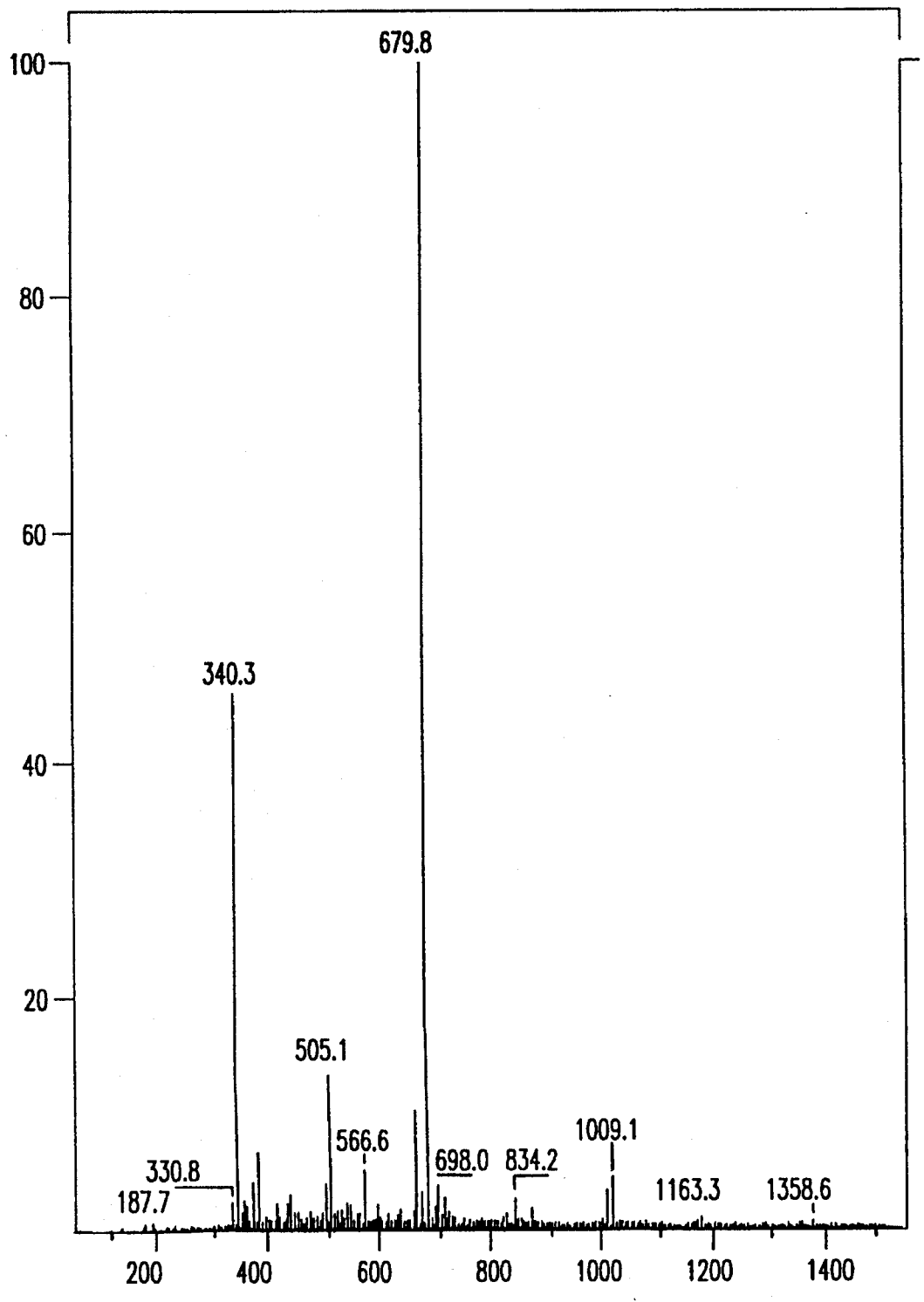
FIG. 2. Mass spectra of the peptide LAYWK-NH$_2$ (SEQ. ID NO: 1) obtained by electrospray (ESI) ionization on a Finnigan MAT TSQ-700 Mass Spectrometer. A. Spectrum of the peptide. B. Spectrum of the deuterium exchanged peptide.
Figure 2B:
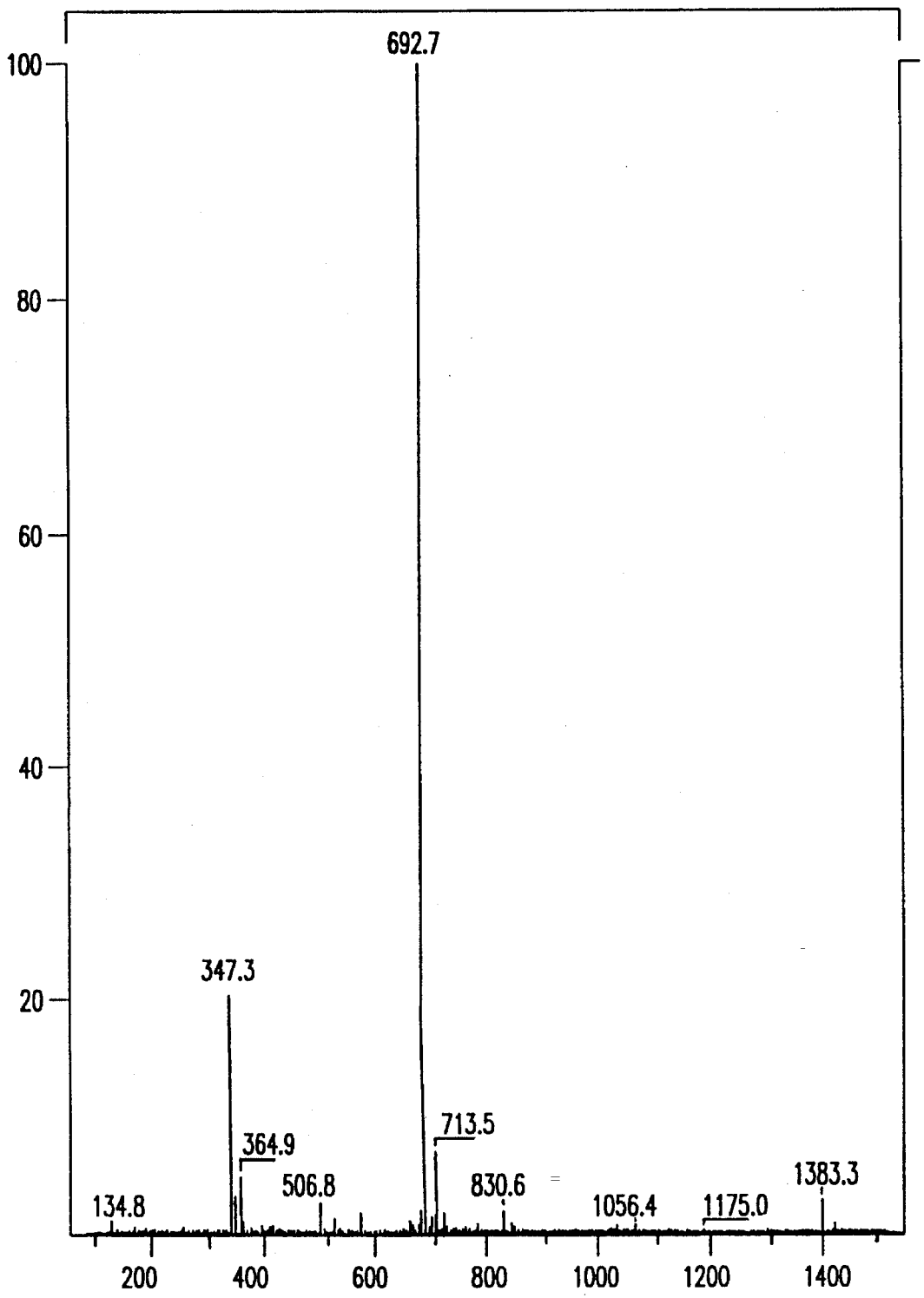
Figure 3A:
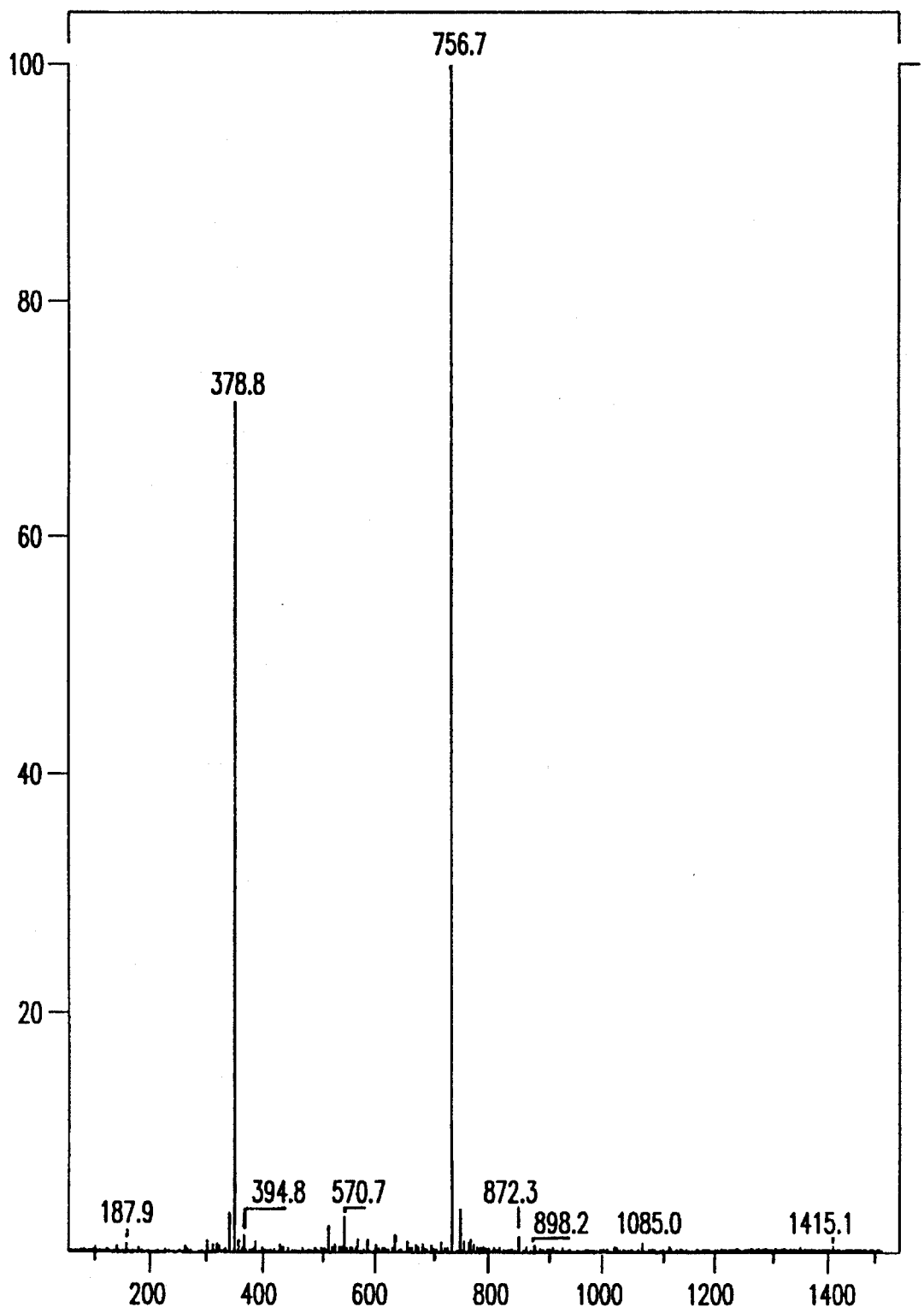
FIG. 3. ESI mass spectra of the peptide WNYFK-NH$_2$ (SEQ. ID NO: 2) before (A) and after (B) deuterium exchange. Procedures and conditions were identical to those used for FIG. 2.
Figure 3B:
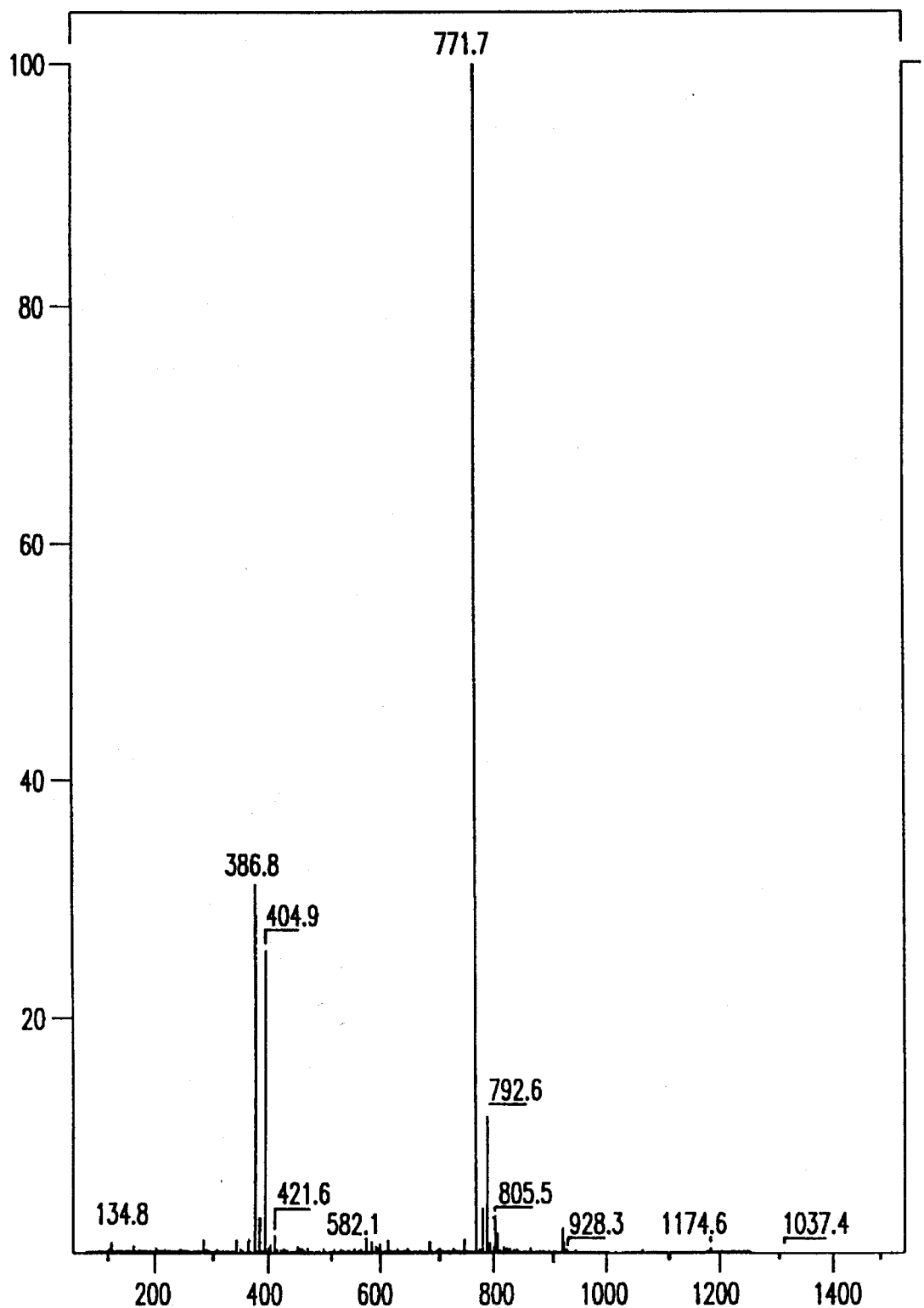
Figure 4A:
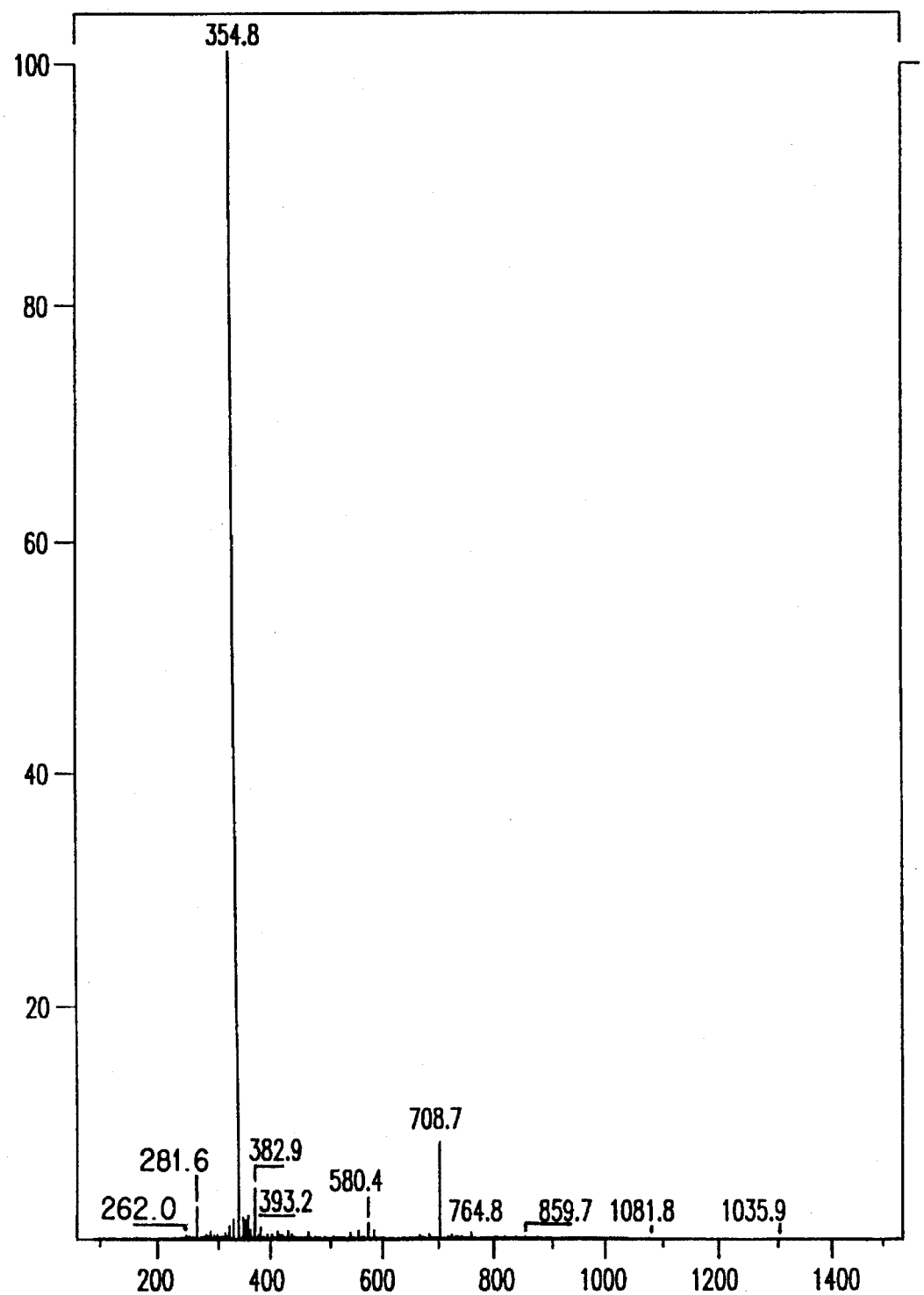
FIG. 4. ESI mass spectra of the peptide KFWKT-NH$_2$ (SEQ. ID NO: 3) before (A) and after (B) deuterium exchange. Procedures and conditions were identical to those used for FIG. 2.
Figure 4B:
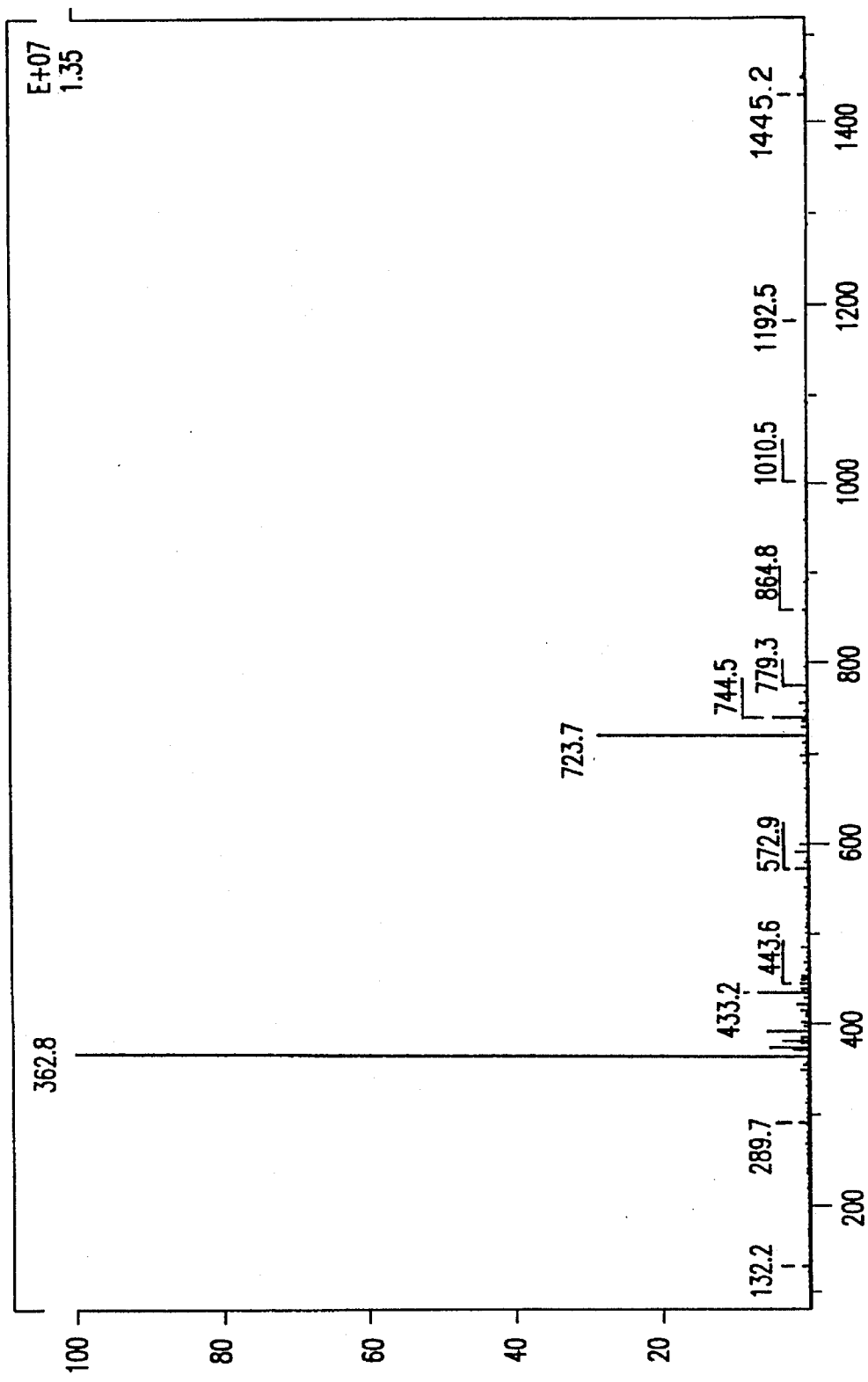

FIG. 2A shows ESI spectrum of peptide LAYWK-$NH_2$ (SEQ. ID NO: 1) and FIG. 2B shows the spectrum of the same peptide after dissolution in 50% $D_2O$/deuterated methanol (concentration is 20 pmol/μl for both peptides). Two peaks—singly charged (679.8) and doubly charged (340.3)—are observed in spectrum of intact peptide (FIG. 2A). The ESI spectrum of the peptide dissolved in deuterated solvents (FIG. 2B) shows molecular ion peaks are shifted by 13 (for the singly charged ion) and 7 (for the doubly charged ion), relative to peaks from the intact peptide. This corresponds to 12 exchangeable protons for LAYWK-$NH_2$ (SEQ. ID NO: 1), which coincides with the number of exchangeable protons calculated for this peptide. FIGS. 3A and 3B represent mass spectra of peptide WNYFK-$NH_2$ (SEQ. ID NO: 2) and the same peptide after hydrogen-deuterium exchange. The mass difference between peptide and the peptide after hydrogen-deuterium exchange ((771.7-2)-(756.7-1)=14) gives the number of exchangeable protons, which coincides with calculated number of labile protons for this peptide. FIGS. 4A and 4B show ESI spectra of peptide KFWKT-$NH_2$ (SEQ. ID NO: 3) and the same peptide after dissolution in deuterated solvents. Comparison of these spectra enables determination of the number of exchangeable protons ((723.7-2)-(708.7-1)=14), which coincides with calculated number of labile protons in this peptide.

These results demonstrate that mass spectrometry allows determination of the number of exchangeable hydrogen atoms in a peptide by experimental observation. The observed number of exchangeable hydrogens corresponds to the number of exchangeable hydrogens expected for each of the peptides analyzed. Thus, this analysis can be used to exclude from theoretical possibilities of peptide compositions or sequences those which are not consistent with the number of labile hydrogens. This selection is based solely on the experimentally determined molecular weight and number of exchangeable protons.

EXAMPLE: SEQUENCE ANALYSIS WITH SEQUENTIALLY TRUNCATED PEPTIDES

This example demonstrates that a peptide for which a "synthetic history" is provided in the form of a set of sequentially truncated peptides can be readily sequenced.

Figure 5A:
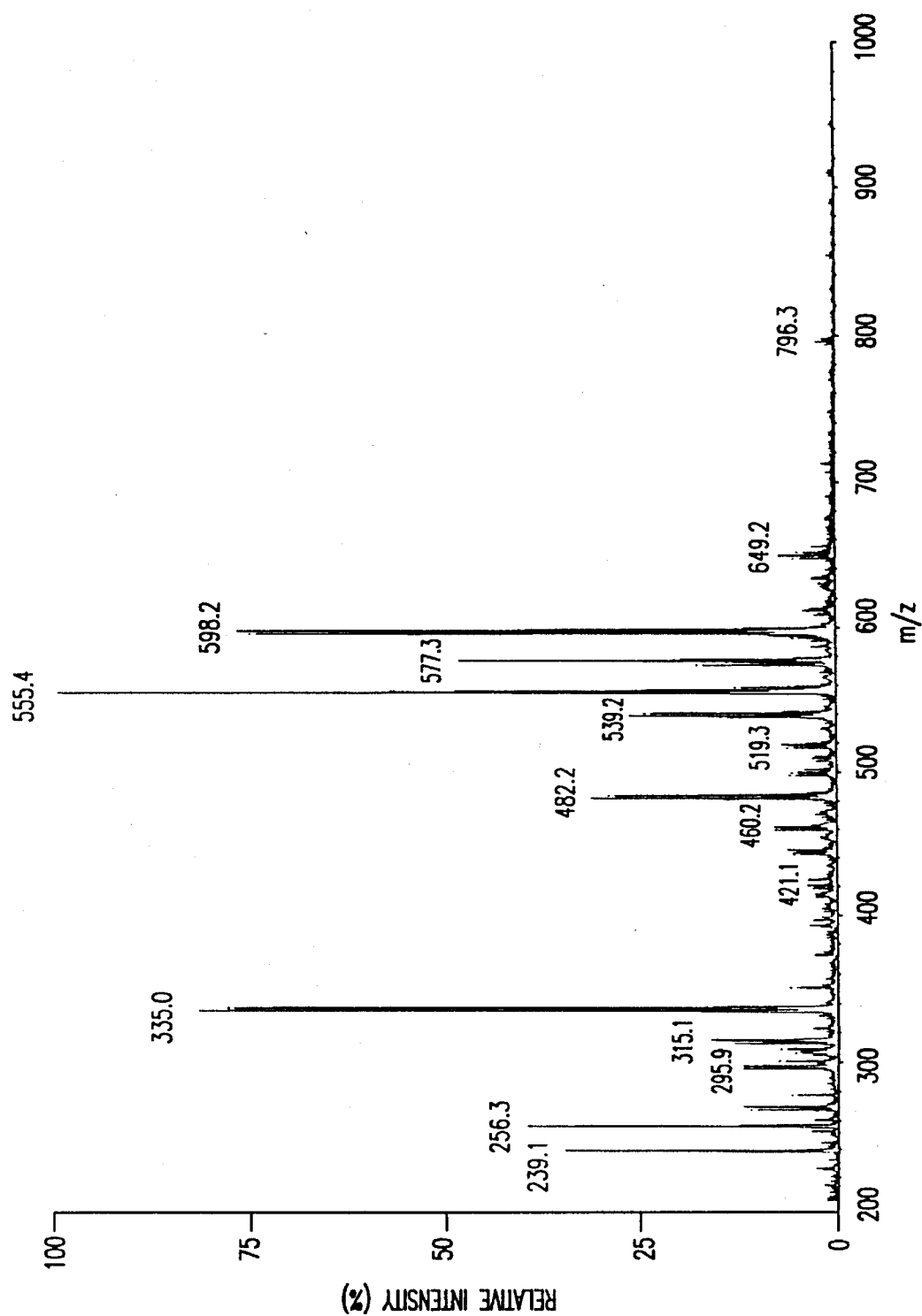
FIG. 5. ESI mass spectra of the peptide Tyr-Gly-Gly-Phe-Leu-NH$_2$ (SEQ. ID NO: 4) and bromobenzoylated sequentially truncated fragments thereof. A. Observed ion peaks of full mass spectrum of peptide. B. Expanded view of the mass spectrum in A from mass number 568 to 584, showing the molecular ions of the peptide and the bromobenzoylated derivative BrBz-Gly-Gly-Phe-Leu-NH$_2$ (SEQ. ID NO: 5). C. Expanded view of the mass spectrum in A from 280 to 360 MW. The apparent doublet peaks corresponding to the bromine isotopes for peptide BrBz-Leu-NH$_2$ (M+Na) (335/337) and BrBz-Leu-NH$_2$ (M+H) (313.1/315.1) are evident.
Figure 5B:
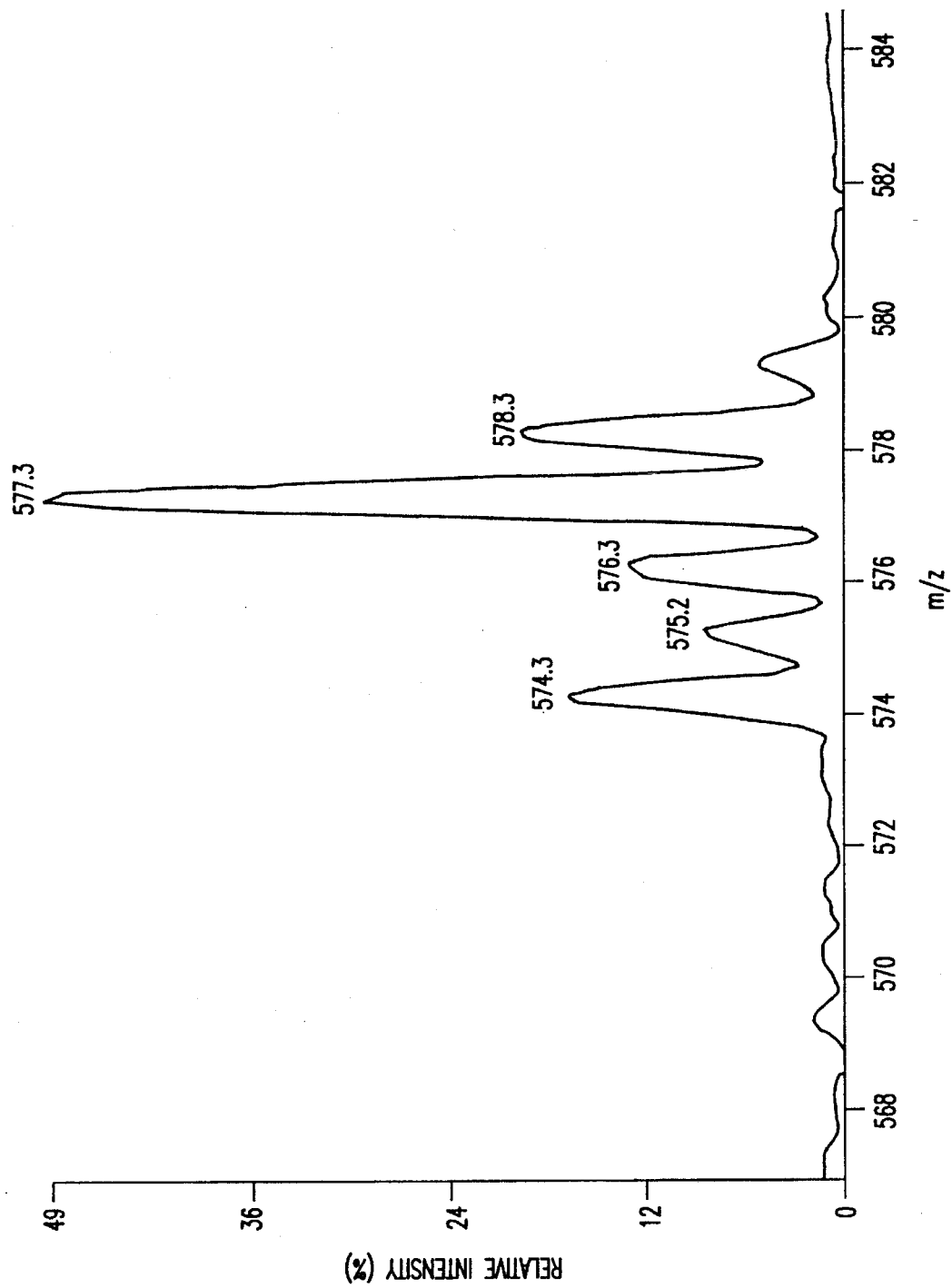
Figure 5C:
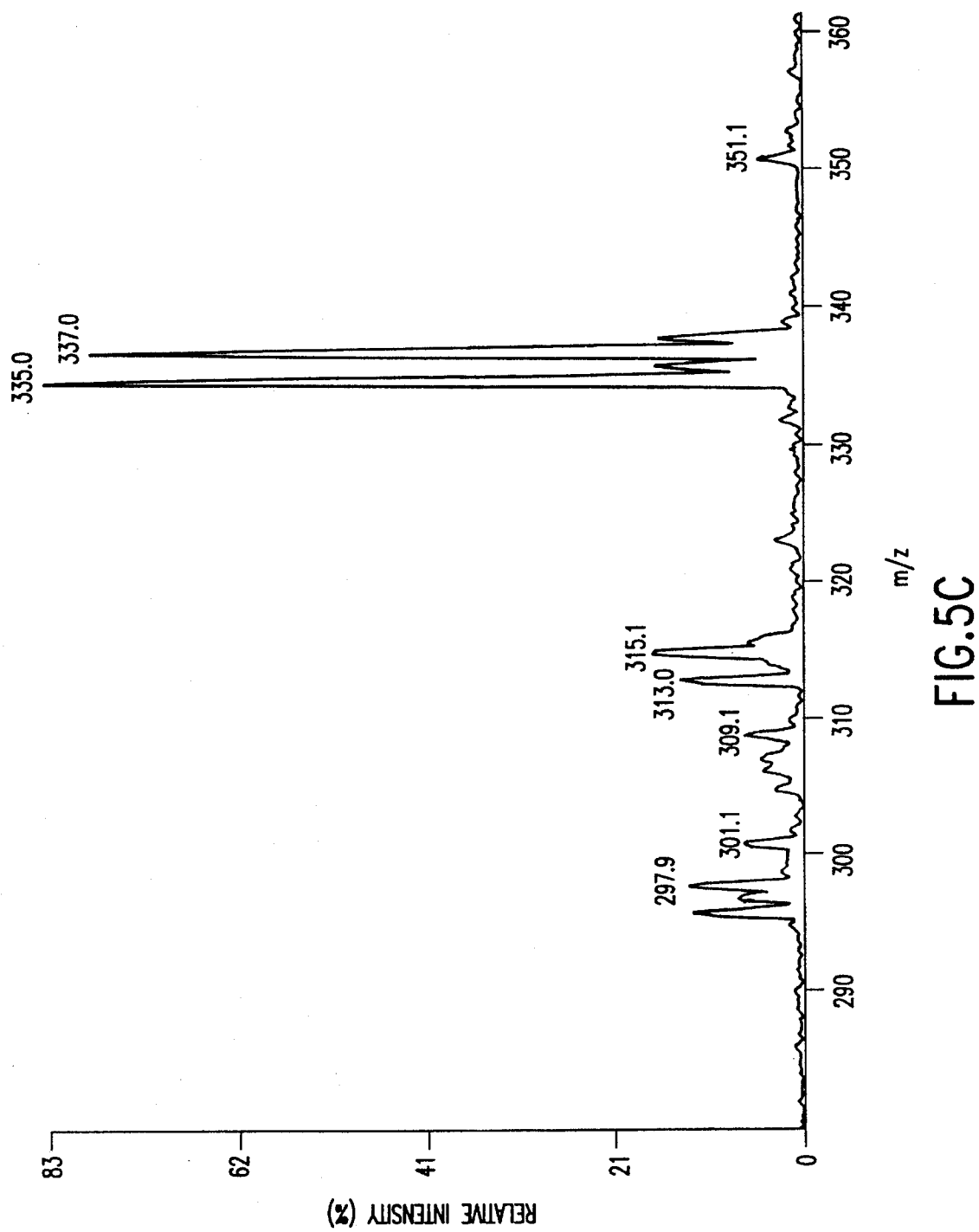

The peptide Tyr-Gly-Gly-Phe-Leu-$NH_2$ (SEQ. ID NO: 4) was synthesized using standard techniques, and a mixture of all synthetic fragments containing amino terminal 3-bromobenzoyl group was generated. The obtained mass spectra of this mixture is shown in FIG. 5. FIG. 5A shows that entire spectrum of the mixture. FIG. 5B is an expanded view of FIG. 5A from MW 568 to 584. FIG. 5C is an expanded view of FIG. 5A from MW 280 to 360. The fragments containing bromine atoms are clearly identifiable since they appear as doublets differing by 2 mass units. Interpretation of the peaks follows:

TABLE 6

Interpretation of Mass Spectra Peaks (SEQ. ID NOS: 4–5)

| Peptide | Observed Mass | |
|---|---|---|
|  | (M + H) | (M + Na) |
| Tyr—Gly—Gly—Phe—Leu—$NH_2$[1] | 555.4 | 577.3 |
| BrBz—Gly—Gly—Phe—Leu—$NH_2$[2] | 574.3/576.3 | 596.2/598.2 |
| BrBz—Gly—Phe—Leu—$NH_2$ | 517.3/519.3 | 539.2/541.2 |
| BrBz—Phe—Leu—$NH_2$ | 460.2/462.2 | 482.2/484.2 |
| BrBz—Leu—$NH_2$ | 313.1/315.1 | 335.0/337.0 |

[1]SEQ. ID NO: 4
[2]SEQ. ID NO: 5

The difference from first and second doublet (from the highest mass) is 57, which corresponds to Gly. The second difference is again 57, i.e., again Gly. The last difference between doublets is 147, which corresponds to Phe. The molecular weight of the last doublet corresponds only to Leu or Ile, and the difference between the molecular ion peak (singlet) and the doublet with the highest molecular weight (after subtraction of BrBz group) is 163, which corresponds to Tyr. Therefore, from these data, the sequence Tyr-Gly-Gly-Phe-Leu/Ile (SEQ. ID NO: 47) can be easily deduced.

EXAMPLE: A MODEL DETERMINATION OF A PEPTIDE SEQUENCE FROM MASS SPECTROMETRIC DATA

Information about number of exchangeable protons reduces radically number of different amino acid compositions corresponding to the determined molecular weight. It becomes reasonable to evaluate candidate sequences for every possible composition (especially for peptides up to 10 residues in length). One way to determine the amino acid sequence from mass spectometric data is to calculate all permutations of the constituent amino acids to create all possible sequences, and then compare fragment ions calculated for every sequence with experimental peaks (see Matsuo, 1981, Biomed. Mass Spectrom. 8:137; Sakurai, 1984, Biomed. Mass Spectrom. 11:3 96). However, even with the advantage of a limited number of compositions, this process is very time consuming.

Instead of generating all possible sequences, the present Example demonstrates a further simplification of the problem by calculating fragment ions for every composition instead of for every sequence. The number of possible fragments is $20^n-1$ for an n-residue peptide, which is considerably less than number of possible sequences, which is $20^n$ for peptides that contain the 20 natural amino acids. Calculated fragment ions are evaluated for a match with experimental peaks. The calculated fragment ions relate only to amino acid composition; any order of symbols in output fragment ions is arbitrary and does not reflect sequence information. However, the information about fragment composition can be used to deduce the sequence of the peptide in a straight-forward manner.

METHOD

The algorithm for this procedure is as follows:

1) calculate all possible fragments from a composition under consideration;
2) evaluate fragments calculated above as N-terminal fragments by adding appropriate offsets to the calculated molecular weights of the fragments, which are equal to sum of molecular weights of constituent residues. For example, in electrospray low energy CID (collision induced dissociation) experiments, the A, B, A-17, B-17 series of N-terminal ions can be formed and appropriate offsets will be the following:
   offset=Nterminal group for B series;
   offset=Nterminal group−17 for B−17 series;
   offset=Nterminal group−28 for A series; and
   offset=Nterminal group−2817 for A−17 series.
3) compare mass values of putative N-terminal ions calculated in (2) with experimental peaks and save those that match fragment ion peaks observed experimentally;
4) evaluate fragments calculated above (in step 1) as C-terminal fragments by adding appropriate offsets to the calculated molecular weights of the fragments. For example, in electrospray low energy CID experiments, the Y" and Y"−17 series of C-terminal ions can be formed and appropriate offsets will be the following:
   offset=C-terminal group +2 for Y" series;
   offset=C-terminal group +2−17 for Y"−17 series;
5) compare mass values of putative C-terminal ions calculated in (4) with experimental peaks and save those which match fragment ion peaks observed experimentally;
6) reexpress C-terminal fragment ions that have been saved as complementary N-terminal composition fragments. This involves deducing possible N-terminal fragment based on the observed C-terminal fragment. A fragment is complementary if the number of amino acid residues of every type in the C-terminal fragment plus the number of residues in complementary N-terminal fragment is equal to total number of residues of the composition under consideration. Reexpression of all the C-terminal fragment allow deduction of a sequence or probable sequence. The same process can be performed with the save N-terminal fragments.

Thus in the result of stages 1–6, experimental peaks are matched to calculated fragment ions, and then candidate sequences are created from these fragments. The fragments are arranged in groups such that within every group every next fragment includes the previous one. Thus, in our algorithm, candidate sequences are evaluated for every composition calculated by the first procedure. The score for every candidate sequence is equal to number of fragment ions that match experimentally observed fragment ions, plus number of matching spectrum amino acid immonium ions divided by two.

RESULTS

A hypothetical example illustrates this algorithm. Input data: MW=360;
   number of residues n=3
   number of exchangeable protons D=10;
   no modifications of N- and C-terminal groups;
   hypothetical peaks observed in spectra (electrospray low energy CID): 361, 290, 175.

Ten compositions are consistent with molecular weight (360) and the number of residues (3) are possible:

1. N;M;P
2. N;N;N
3. L or I; K or Q; T
4. L or I; N; D
5. V; R; S
6. V; K or Q; D
7. V; N; E
8. A; R; D
9. G; R; E
10. V; G; W

Three compositions consistent with MW, n and the number of exchangeable protons (D) are possible:

1. V; S; R
2. A; R; D
3. E; G; R

All possible fragments and corresponding ions for each of three compositions are listed in tables below. Ions which coincide with those in the hypothetically observed experimental ions are indicated with boldface type):

1. Composition (VSR) (here and below, parenthesis mean that order of symbols in fragments does not reflect their sequence, i.e., it is just composition):

| Possible Fragments | N-terminal ions | | | | C-terminal ions | |
|---|---|---|---|---|---|---|
| | A | A-17 | B | B-17 | Y" | Y"-17 |
| V | 72 | 55 | 100 | 83 | 118 | 101 |
| S | 60 | 43 | 88 | 71 | 106 | 89 |
| R | 129 | 112 | 157 | 140 | 175 | 158 |
| (VS) | 159 | 142 | 187 | 170 | 205 | 188 |
| (VR) | 228 | 221 | 256 | 239 | 274 | 257 |
| (SR) | 216 | 199 | 244 | 227 | 262 | 245 |
| (VSR) | 315 | 298 | 343 | 326 | 361 | 344 |

2. Composition (ARD)

| Possible Fragment | N-terminal ions | | | | C-terminal ions | |
|---|---|---|---|---|---|---|
| | A | A-17 | B | B-17 | Y" | Y"-17 |
| A | 44 | 27 | 72 | 55 | 90 | 73 |
| R | 129 | 112 | 157 | 140 | 175 | 158 |
| D | 88 | 71 | 116 | 99 | 134 | 117 |
| (AR) | 200 | 183 | 228 | 211 | 246 | 229 |
| (AD) | 159 | 142 | 187 | 170 | 205 | 188 |
| (RD) | 244 | 227 | 272 | 255 | 290 | 273 |
| (ARD) | 315 | 298 | 343 | 326 | 361 | 344 |

3. Composition EGR

| Possible Fragments | N-terminal ions | | | | C-terminal ions | |
|---|---|---|---|---|---|---|
| | A | A-17 | B | B-17 | Y" | Y"-17 |
| E | 102 | 85 | 130 | 113 | 148 | 131 |
| G | 30 | 13 | 58 | 41 | 76 | 59 |
| R | 129 | 112 | 157 | 140 | 175 | 158 |
| (EG) | 159 | 142 | 187 | 170 | 205 | 188 |
| (ER) | 258 | 241 | 286 | 269 | 304 | 287 |
| (RG) | 186 | 169 | 214 | 197 | 232 | 215 |
| (EGR) | 315 | 298 | 343 | 326 | 361 | 344 |

It is clear from tables that there is no N-terminal ion in any of three compositions that matches the experimental peaks. The C-terminal ions that match experimental peaks and corresponding fragments which should be saved for building candidate sequences are the following:

composition VSR—R; (VSR)

composition ARD—R; (RD); (ARD)

composition EGR—R; (EGR).

The next step is reexpression of the C-terminal ions into N-terminal, i.e., deduce of possible N-terminal ions:

| C-terminal ion | reexpressed ion |
|---|---|
| composition VSR | |
| R | (VS) |
| (VSR) | (VSR) |
| composition ARD | |
| R | (AD) |
| (RD) | A |
| (ARD) | (ARD) |
| composition EGR | |
| R | (EG) |
| (EGR) | (EGR) |

The reexpressed fragments are those from which we start to build sequences:

Composition VSR: fragment (VS) can be inserted into fragment (VSR), hence the candidate sequence is (VS)R.

Composition ARD: fragment A can be inserted into (AD), hence A is the N-terminal amino acid residue and D is the second residue; (AD) can be inserted into (ADR), hence R is the last residue in sequence of the peptide; and the candidate sequence is ADR.

Composition EGR: fragment EG can be inserted into (EGR), hence probable sequence is (EG)R.

The output of our algorithm is:

| composition | sequence | score |
|---|---|---|
| (VRS) | (VS)R | 1 |
| (ARD) | ADR | 2 |
| (EGR) | (GE)R | 1 |

The right column in the output is the score of every candidate sequence, which is equal to number of fragment ions that match experimental ions (molecular ion not included). In our example, for the sequence (VS)R, only one ion matches an experimental ion ($Y''_1$ 175). For candidate sequence ADR, two ions (175 and 290). For candidate sequence (EG)R, one ion (175) matches.

Thus, the algorithm builds chains of fragments (using as building blocks N-terminal fragments and C-terminal ions reexpressed as N-terminal) starting with fragments with a minimum number of residues, step by step, checking on every next step if there are fragments with one more residue than the previous one and if the previous unit of chain can be inserted into the next ("can be inserted" means that all the amino acids of (k-1) unit present in amino acid composition of k unit). If this condition is fulfilled, the program extends the chain one more unit and so on. If there are no fragments, but only one residue longer than the previous unit of chain, the program checks two residue long fragments, and so on.

Consideration of only N-terminal fragments allows build up of candidate sequences from N-terminus to C-terminus. For example, the step by step evaluation leading to chain A-(AB) - (ABC) determines "A" as N-terminal residue, "B" as the second residue and "C" as the third one and determines candidate sequence ABC.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for determining the sequence of a peptide comprising:
   (a) determining the possible amino acid compositions of a peptide according to a method comprising the following steps:
   (i) determining the mass of a peptide from a mass spectrum of the peptide;
   (ii) determining the mass of a first derivative of the peptide;
   (iii) determining the number of reactive moieties in the peptide from the difference between the mass of the peptide and the mass of the first derivative of the peptide; and
   (iv) eliminating compositions that do not contain the number of reactive moieties determined in step (iii);
   (b) calculating all possible fragments consistent with the amino acid compositions determined in step (a);
   (c) evaluating the calculated fragments of step (b) as N-terminal fragments and as C-terminal fragments;
   (d) selecting N-terminal and C-terminal fragment ions from fragments calculated in step (b) that match a daughter ion peak found in the mass spectrum of the peptide; and
   (e) constructing candidate sequences from fragment ions selected in step (d).

2. The method of claim 1 in which the first derivative of the peptide is hydrogen-deuterium exchanged peptide.

3. The method of claim 1 in which the first derivative of the peptide is selected from the group consisting of acylated peptide, esterified peptide, 9,10-ephenanthroquinonylated peptide, brominated peptide, iodinated peptide, and alkylated peptide or acylated peptide.

* * * * *

UNITED STATES PATENT AND TRADEMARK OFFICE
CERTIFICATE OF CORRECTION

PATENT NO. : 5,470,753

DATED : November 28, 1995

INVENTOR(S) : Sepetov et al.

It is certified that error appears in the above-identified patent and that said Letters Patent is hereby corrected as shown below:

At col. 4,     line 62, change "MATTSQ-700" to -- MAT TSQ-700 --.

At col. 13,    line 23, change "Co-CO" to -- C$a$-CO --.

At col. 16,    line 13, change "Consistent" to -- consistent --.

At col. 23,    line 53, change "2817" to -- 28-17 --.

At FIG.1A,    change "a = 0" to -- a = 1 --.

Signed and Sealed this

Eleventh Day of November, 1997

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Leu  Ala  Tyr  Trp  Lys
1                    5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
Trp  Asn  Tyr  Phe  Lys
1                    5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Lys  Phe  Trp  Lys  Thr
1                    5
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Tyr  Gly  Gly  Phe  Leu
1                    5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa
        / note="BrBz"

( x i ) SEQUENCE DESCRIPTION: SEQ ID NO:5:

```
Xaa  Gly  Gly  Phe  Leu
1                   5
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
Val  Asn  Ser  Gln  Ile  Gln  Pro  Gly  Gln  Val  Val  Val  Phe
1                   5                        10
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
Gly  Gly  Val  Ser  Gln  Ile  Gln  Pro  Gly  Gln  Val  Val  Val  Phe
1                   5                        10
```

( 2 ) INFORMATION FOR SEQ ID NO:8:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

```
Asn  Val  Ser  Gln  Ile  Gln  Pro  Gly  Gln  Val  Val  Val  Phe
1                   5                        10
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:9:

```
Val  Ser  Gly  Gly  Gln  Ile  Gln  Pro  Gly  Gln  Val  Val  Val  Phe
1                   5                        10
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Modified-site
        ( B ) LOCATION: 4
        ( D ) OTHER INFORMATION: /label=Xaa
                / note="UNKNOWN AMINO ACID"

( x i ) SEQUENCE DESCRIPTION: SEQ ID NO:10:

```
Val  Asn  Ser  Xaa  Gln  Gln  Pro  Gly  Gln  Val  Val  Phe
1              5                        10
```

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Gly  Arg  Ser  Gln  Ile  Gln  Pro  Gly  Gln  Val  Val  Val  Phe
1              5                        10
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Gly  Gly  Ala  Asp  Gln  Ile  Gln  Pro  Gly  Gln  Val  Val  Val  Phe
1              5                        10
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
                / note="UNKNOWN AMINO ACID"

( x i ) SEQUENCE DESCRIPTION: SEQ ID NO:13:

```
Xaa  Ala  Asp  Gln  Ile  Gln  Pro  Gly  Gln  Val  Val  Val  Phe
1              5                        10
```

( 2 ) INFORMATION FOR SEQ ID NO:14:

( i ) SEQUENCE CHARACTERISTICS:

(A) LENGTH: 13 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:14:

Asn Ala Asp Gln Ile Gln Pro Gly Gln Val Val Val Phe
1               5                   10

(2) INFORMATION FOR SEQ ID NO:15:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:15:

Gly Gln Asp Gln Ile Gln Pro Gly Gln Val Val Val Phe
1               5                   10

(2) INFORMATION FOR SEQ ID NO:16:

(i) SEQUENCE CHARACTERISTICS:
    (A) LENGTH: 13 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:16:

Ser Pro Asp Gln Ile Gln Pro Gly Gln Val Val Val Phe
1               5                   10

(2) INFORMATION FOR SEQ ID NO:17:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:17:

Ser Val Gly Gly Gln Ile Gln Pro Gly Gln Val Val Val Phe
1               5                   10

(2) INFORMATION FOR SEQ ID NO:18:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:18:

Gly Gly Glu Gly Gln Ile Gln Pro Gly Gln Val Val Val Phe
1               5                   10

(2) INFORMATION FOR SEQ ID NO:19:

( i ) SEQUENCE CHARACTERISTICS:
  ( A ) LENGTH: 13 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:19:

Asn Glu Gly Gln Ile Gln Pro Gly Gln Val Val Val Phe
1               5                   10

( 2 ) INFORMATION FOR SEQ ID NO:20:

( i ) SEQUENCE CHARACTERISTICS:
  ( A ) LENGTH: 13 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:20:

Ser Arg Gly Gln Ile Gln Pro Gly Gln Val Val Val Phe
1               5                   10

( 2 ) INFORMATION FOR SEQ ID NO:21:

( i ) SEQUENCE CHARACTERISTICS:
  ( A ) LENGTH: 13 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:21:

Val Asn Ser Gln Ile Gln Pro Gly Gln Val Thr Pro Phe
1               5                   10

( 2 ) INFORMATION FOR SEQ ID NO:22:

( i ) SEQUENCE CHARACTERISTICS:
  ( A ) LENGTH: 13 amino acids
  ( B ) TYPE: amino acid
  ( C ) STRANDEDNESS: unknown
  ( D ) TOPOLOGY: unknown ( i i ) MOLECULE TYPE: peptide ( i x ) FEATURE:
  ( A ) NAME/KEY: Modified-site
  ( B ) LOCATION: 5
  ( D ) OTHER INFORMATION: /label=Xaa
    / note="UNKNOWN AMINO ACID"

( x i ) SEQUENCE DESCRIPTION: SEQ ID NO:22:

Gly Gly Val Ser Xaa Gln Pro Gly Gln Val Val Phe
1               5                   10

( 2 ) INFORMATION FOR SEQ ID NO:23:

( i ) SEQUENCE CHARACTERISTICS:
  ( A ) LENGTH: 13 amino acids
  ( B ) TYPE: amino acid
  ( C ) STRANDEDNESS: unknown
  ( D ) TOPOLOGY: unknown ( i i ) MOLECULE TYPE: peptide ( i x ) FEATURE:

( A ) NAME/KEY: Modified-site
( B ) LOCATION: 4
( D ) OTHER INFORMATION: /label=Xaa
   / note="UNKNOWN AMINO ACID"

( x i ) SEQUENCE DESCRIPTION: SEQ ID NO:23:

```
Asn  Val  Ser  Xaa  Gln  Gln  Pro  Gly  Gln  Val  Val  Val  Phe
1                  5                        10
```

( 2 ) INFORMATION FOR SEQ ID NO:24:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:24:

```
Asp  Gln  Gly  Gln  Ile  Gln  Pro  Gly  Gln  Val  Val  Val  Phe
1                  5                        10
```

( 2 ) INFORMATION FOR SEQ ID NO:25:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:25:

```
Gln  Asp  Gly  Gln  Ile  Gln  Pro  Gly  Gln  Val  Val  Val  Phe
1                  5                        10
```

( 2 ) INFORMATION FOR SEQ ID NO:26:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:26:

```
Gly  Ala  Gln  Gly  Ala  Gly  Gln  Val  Gly  Glu  Phe
1                  5                        10
```

( 2 ) INFORMATION FOR SEQ ID NO:27:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:27:

```
Gly  Ala  Gln  Gly  Gln  Ala  Gly  Val  Gly  Glu  Phe
1                  5                        10
```

( 2 ) INFORMATION FOR SEQ ID NO:28:

( i ) SEQUENCE CHARACTERISTICS:
        ( A ) LENGTH: 10 amino acids (B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:28:

Gly Ala Gln Gly Gln Gln Val Gly Glu Phe
1               5                   10

(2) INFORMATION FOR SEQ ID NO:29:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:29:

Gly Ala Gln Gly Gln Gln Gly Val Glu Phe
1               5                   10

(2) INFORMATION FOR SEQ ID NO:30:

(i) SEQUENCE CHARACTERISTICS:
    (A) LENGTH: 10 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:30:

Ala Ala Asn Gly Gln Gln Val Gly Glu Phe
1               5                   10

(2) INFORMATION FOR SEQ ID NO:31:

(i) SEQUENCE CHARACTERISTICS:
    (A) LENGTH: 11 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:31:

Ala Gly Gln Gly Ala Gly Gln Val Gly Glu Phe
1               5                   10

(2) INFORMATION FOR SEQ ID NO:32:

(i) SEQUENCE CHARACTERISTICS:
    (A) LENGTH: 11 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:32:

Ala Gly Gln Gly Gln Ala Gly Val Gly Glu Phe
1               5                   10

(2) INFORMATION FOR SEQ ID NO:33:

(i) SEQUENCE CHARACTERISTICS:

(A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:33:

Ala Gly Gln Gly Gln Gln Val Gly Glu Phe
    1               5                   10

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:34:

Gln Gln Gly Ala Gly Gln Val Gly Glu Phe
    1               5                   10

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:35:

Gln Gln Gly Gln Ala Gly Val Gly Glu Phe
    1               5                   10

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:36:

Gln Gln Gly Gln Gln Val Gly Glu Phe
    1               5

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:37:

Asn Ala Ala Gly Gln Gln Val Phe Glu Gly
    1               5                   10

(2) INFORMATION FOR SEQ ID NO:38:

( i ) SEQUENCE CHARACTERISTICS:
    ( A ) LENGTH: 11 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:38:

```
Ala Gly Gly Ala Gly Gln Gln Val Gly Glu Phe
1               5                   10
```

( 2 ) INFORMATION FOR SEQ ID NO:39:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:39:

```
Gly Ala Gly Ala Gly Gln Gln Val Gly Glu Phe
1               5                   10
```

( 2 ) INFORMATION FOR SEQ ID NO:40:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:40:

```
Gly Ala Gly Ala Gly Gln Gln Gly Val Glu Phe
1               5                   10
```

( 2 ) INFORMATION FOR SEQ ID NO:41:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:41:

```
Gln Gly Ala Gly Gln Gln Val Gly Glu Phe
1               5                   10
```

( 2 ) INFORMATION FOR SEQ ID NO:42:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:42:

```
Ala Gly Gln Gly Gln Gln Gly Val Glu Phe
1               5                   10
```

( 2 ) INFORMATION FOR SEQ ID NO:43:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:43:

Gln Gln Gly Gln Gln Gly Val Glu Phe
1               5

( 2 ) INFORMATION FOR SEQ ID NO:44:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:44:

Ala Ala Asn Gly Gln Gln Val Trp Phe
1               5

( 2 ) INFORMATION FOR SEQ ID NO:45:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:45:

Gln Gln Gly Gln Ala Asn Val Glu Phe
1               5

( 2 ) INFORMATION FOR SEQ ID NO:46:

( i ) SEQUENCE CHARACTERISTICS:
    ( A ) LENGTH: 9 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:46:

Lys Lys Gly Glu Lys Val Gly Glu Phe
1               5

( 2 ) INFORMATION FOR SEQ ID NO:47:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( i x ) FEATURE:
    ( A ) NAME/KEY: Modified-site
    ( B ) LOCATION: 5
    ( D ) OTHER INFORMATION: /label=Xaa
        / note="Leu/Ile"

( x i ) SEQUENCE DESCRIPTION: SEQ ID NO:47:

Tyr Gly Gly Phe Xaa
1               5